(12) United States Patent
Parihar et al.

(10) Patent No.: US 9,737,300 B2
(45) Date of Patent: Aug. 22, 2017

(54) ELECTROSURGICAL DEVICE WITH DISPOSABLE SHAFT HAVING RACK AND PINION DRIVE

(71) Applicant: Ethicon Endo-Surgery, Inc., Cincinnati, OH (US)

(72) Inventors: Shailendra K. Parihar, Mason, OH (US); Barry C. Worrell, Centerville, OH (US); David T. Martin, Milford, OH (US); William J. White, West Chester, OH (US); Gregory W. Johnson, IV, Milford, OH (US)

(73) Assignee: Ethicon LLC, Guaynabo, PR (US)

( * ) Notice: Subject to any disclaimer, the term of this patent is extended or adjusted under 35 U.S.C. 154(b) by 117 days.

(21) Appl. No.: 13/798,735

(22) Filed: Mar. 13, 2013

(65) Prior Publication Data

US 2014/0276723 A1 Sep. 18, 2014

(51) Int. Cl.
| | |
|---|---|
| A61B 17/072 | (2006.01) |
| A61B 17/00 | (2006.01) |
| A61B 17/29 | (2006.01) |
| A61B 17/32 | (2006.01) |
| A61B 18/14 | (2006.01) |
| A61B 34/30 | (2016.01) |

(52) U.S. Cl.
CPC ........ *A61B 17/07207* (2013.01); *A61B 34/30* (2016.02); *A61B 17/320092* (2013.01); *A61B 18/1445* (2013.01); *A61B 2017/00398* (2013.01); *A61B 2017/00477* (2013.01); *A61B 2017/2903* (2013.01); *A61B 2017/2905* (2013.01); *A61B 2017/2923* (2013.01); *A61B 2017/2927* (2013.01); *A61B 2018/1455* (2013.01); *A61B 2034/301* (2016.02)

(58) Field of Classification Search
CPC ................ A61B 2017/2943; A61B 2017/2923
USPC .......................................................... 606/41
See application file for complete search history.

(56) References Cited

U.S. PATENT DOCUMENTS 5,792,135 A     8/1998  Madhani et al.
5,817,084 A  *  10/1998  Jensen ................... B25J 9/1065
                                                            606/1
(Continued)

FOREIGN PATENT DOCUMENTS

JP   WO 2013/155155 A2   10/2013
WO   WO 2008/045333 A2    4/2008

OTHER PUBLICATIONS

U.S. Appl. No. 61/550,768, filed Oct. 24, 2011.
(Continued)

*Primary Examiner* — Alyssa M Alter
(74) *Attorney, Agent, or Firm* — Frost Brown Todd LLC

(57) ABSTRACT

An apparatus comprises an end effector, a shaft assembly, and an interface assembly. The end effector is coupled with the shaft assembly. The shaft assembly comprises a translating member extending through the shaft assembly. The interface assembly is operable to engage the shaft assembly and comprises a plurality of drive shafts and a rack. One of the drive shafts is operable to drive the rack along a path that is parallel to the longitudinal axis of the shaft assembly. A plurality of racks may be used to rotate the shaft assembly, articulate the shaft assembly, and/or drive the translating member through the shaft assembly to thereby actuate the end effector.

20 Claims, 30 Drawing Sheets

(56) References Cited

U.S. PATENT DOCUMENTS

| | | | |
|---|---|---|---|
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,500,176 B1 | 12/2002 | Truckai et al. | |
| 6,783,524 B2 * | 8/2004 | Anderson et al. | 606/28 |
| 7,112,201 B2 | 9/2006 | Truckai et al. | |
| 7,125,409 B2 | 10/2006 | Truckai et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,380,696 B2 | 6/2008 | Shelton, IV et al. | |
| 7,381,209 B2 | 6/2008 | Truckai et al. | |
| 7,404,508 B2 | 7/2008 | Smith et al. | |
| 7,455,208 B2 | 11/2008 | Wales et al. | |
| 7,506,790 B2 | 3/2009 | Shelton, IV | |
| 7,524,320 B2 | 4/2009 | Tierney et al. | |
| 7,549,564 B2 | 6/2009 | Boudreaux | |
| 7,559,450 B2 | 7/2009 | Wales et al. | |
| 7,654,431 B2 | 2/2010 | Hueil et al. | |
| 7,691,098 B2 | 4/2010 | Wallace et al. | |
| 7,780,054 B2 | 8/2010 | Wales | |
| 7,784,662 B2 | 8/2010 | Wales et al. | |
| 7,798,386 B2 | 9/2010 | Schall et al. | |
| 7,806,891 B2 | 10/2010 | Nowlin et al. | |
| 7,824,401 B2 | 11/2010 | Manzo et al. | |
| 8,461,744 B2 | 6/2013 | Wiener et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,602,288 B2 | 12/2013 | Shelton, IV et al. | |
| 8,616,431 B2 | 12/2013 | Timm et al. | |
| 9,204,923 B2 | 12/2015 | Manzo et al. | |
| 2006/0064085 A1 * | 3/2006 | Schechter | A61B 18/1445 606/50 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2011/0082486 A1 | 4/2011 | Messerly et al. | |
| 2011/0087212 A1 | 4/2011 | Aldridge et al. | |
| 2011/0087213 A1 | 4/2011 | Messerly et al. | |
| 2011/0087214 A1 | 4/2011 | Giordano et al. | |
| 2011/0087215 A1 | 4/2011 | Aldridge et al. | |
| 2011/0087216 A1 | 4/2011 | Aldridge et al. | |
| 2011/0087217 A1 | 4/2011 | Yates et al. | |
| 2011/0087218 A1 | 4/2011 | Boudreaux et al. | |
| 2011/0295269 A1 | 12/2011 | Swensgard et al. | |
| 2012/0078243 A1 | 3/2012 | Worrell et al. | |
| 2012/0078247 A1 | 3/2012 | Worrell et al. | |
| 2012/0078248 A1 | 3/2012 | Worrell et al. | |
| 2012/0116379 A1 | 5/2012 | Yates et al. | |
| 2012/0138660 A1 | 6/2012 | Shelton, IV | |
| 2012/0199630 A1 | 8/2012 | Shelton, IV et al. | |
| 2012/0199632 A1 | 8/2012 | Spivey et al. | |
| 2012/0203247 A1 | 8/2012 | Shelton, IV et al. | |
| 2013/0012957 A1 | 1/2013 | Shelton, IV et al. | |
| 2013/0023868 A1 | 1/2013 | Worrell et al. | |
| 2013/0030428 A1 | 1/2013 | Worrell et al. | |
| 2013/0267969 A1 | 10/2013 | Martin et al. | |

OTHER PUBLICATIONS

U.S. Appl. No. 61/597,603, filed Feb. 10, 2012.
International Search Report and Written Opinion dated Jun. 1, 2014 for Application No. PCT/US2014/016850, 13 pgs.
International Preliminary Report on Patentability and Written Opinion dated Sep. 15, 2015 for Application No. PCT/US2014/016850, 10 pgs.

* cited by examiner

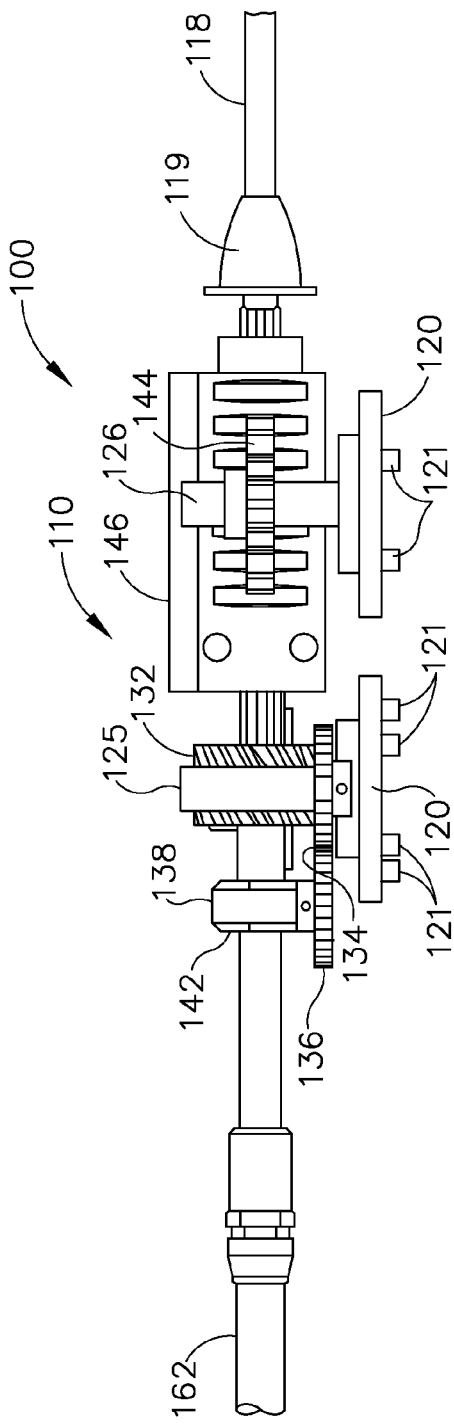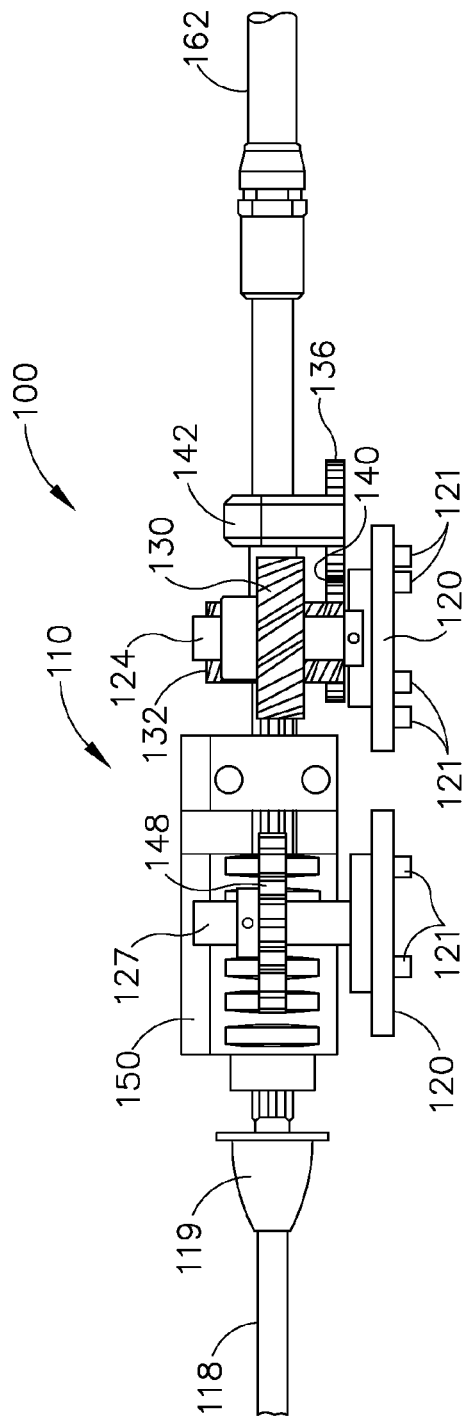
Fig. 12
Fig. 13

ELECTROSURGICAL DEVICE WITH DISPOSABLE SHAFT HAVING RACK AND PINION DRIVE

BACKGROUND

A variety of surgical instruments include a tissue cutting element and one or more elements that transmit radio frequency (RF) energy to tissue (e.g., to coagulate or seal the tissue). An example of an RF electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued on Jan. 27, 2015, the disclosure of which is incorporated by reference herein; U.S. Pub. No. 2012/0116379, entitled "Motor Driven Electrosurgical Device with Mechanical and Electrical Feedback," published May 10, 2012, now U.S. Pat. No. 9,161,803, issued on Oct. 20, 2015, the disclosure of which is incorporated by reference herein; U.S. Pub. No. 2012/0078243, entitled "Control Features for Articulating Surgical Device," published Mar. 29, 2012, the disclosure of which is incorporated by reference herein; U.S. Pub. No. 2012/0078247, entitled "Articulation Joint Features for Articulating Surgical Device," published Mar. 29, 2012, now U.S. Pat. No. 9,402,682, issued on Aug. 2, 2016, the disclosure of which is incorporated by reference herein; U.S. Pub. No. 2013/0030428, entitled "Surgical Instrument with Multi-Phase Trigger Bias," published Jan. 31, 2013, now U.S. Pat. No. 9,089,327, issued on Jul. 28, 2015, the disclosure of which is incorporated by reference herein; and U.S. Pub. No. 2013/0023868, entitled "Surgical Instrument with Contained Dual Helix Actuator Assembly," published Jan. 31, 2013, now U.S. Pat. No. 9,545,253, issued on Jan. 17, 2017, the disclosure of which is incorporated by reference herein.

In addition, a variety of surgical instruments include a shaft having an articulation section, providing enhanced positioning capabilities for an end effector that is located distal to the articulation section of the shaft. Examples of such devices include various models of the ENDOPATH® endocutters by Ethicon Endo-Surgery, Inc., of Cincinnati, Ohio. Further examples of such devices and related concepts are disclosed in U.S. Pat. No. 7,380,696, entitled "Articulating Surgical Stapling Instrument Incorporating a Two-Piece E-Beam Firing Mechanism," issued Jun. 3, 2008, the disclosure of which is incorporated by reference herein; U.S. Pat. No. 7,404,508, entitled "Surgical Stapling and Cutting Device," issued Jul. 29, 2008, the disclosure of which is incorporated by reference herein; U.S. Pat. No. 7,455,208, entitled "Surgical Instrument with Articulating Shaft with Rigid Firing Bar Supports," issued Nov. 25, 2008, the disclosure of which is incorporated by reference herein; U.S. Pat. No. 7,506,790, entitled "Surgical Instrument Incorporating an Electrically Actuated Articulation Mechanism," issued Mar. 24, 2009, the disclosure of which is incorporated by reference herein; U.S. Pat. No. 7,549,564, entitled "Surgical Stapling Instrument with an Articulating End Effector," issued Jun. 23, 2009, the disclosure of which is incorporated by reference herein; U.S. Pat. No. 7,559,450, entitled "Surgical Instrument Incorporating a Fluid Transfer Controlled Articulation Mechanism," issued Jul. 14, 2009, the disclosure of which is incorporated by reference herein; U.S. Pat. No. 7,654,431, entitled "Surgical Instrument with Guided Laterally Moving Articulation Member," issued Feb. 2, 2010, the disclosure of which is incorporated by reference herein; U.S. Pat. No. 7,780,054, entitled "Surgical Instrument with Laterally Moved Shaft Actuator Coupled to Pivoting Articulation Joint," issued Aug. 24, 2010, the disclosure of which is incorporated by reference herein; U.S. Pat. No. 7,784,662, entitled "Surgical Instrument with Articulating Shaft with Single Pivot Closure and Double Pivot Frame Ground," issued Aug. 31, 2010, the disclosure of which is incorporated by reference herein; and U.S. Pat. No. 7,798,386, entitled "Surgical Instrument Articulation Joint Cover," issued Sep. 21, 2010, the disclosure of which is incorporated by reference herein.

Some surgical systems provide robotic control of a surgical instrument. With minimally invasive robotic surgery, surgical operations may be performed through a small incision in the patient's body. A robotic surgical system may be used with various types of surgical instruments, including but not limited to surgical staplers, ultrasonic instruments, electrosurgical instruments, and/or various other kinds of instruments, as will be described in greater detail below. An example of a robotic surgical system is the DAVINCI™ system by Intuitive Surgical, Inc., of Sunnyvale, Calif. By way of further example, one or more aspects of robotic surgical systems are disclosed in the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; and U.S. Pat. No. 7,824,401, entitled "Surgical Tool With Writed Monopolar Electrosurgical End Effectors," issued Nov. 2, 2010, the disclosure of which is incorporated by reference herein.

Additional examples of instruments that may be incorporated with a robotic surgical system are described in U.S. Pub. No. 2013/0012957, entitled "Automated End Effector Component Reloading System for Use with a Robotic System, published Jan. 10, 2013, now U.S. Pat. No. 8,844,789, issued on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, now U.S. Pat. No. 8,820,605, issued on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, now U.S. Pat. No. 8,616,431, issued on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, now U.S. Pat. No. 8,573,461, issued on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, now U.S. Pat. No. 8,602,288, issued on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, now U.S. Pat. No. 9,301,759, issued on Apr. 5, 2016, the disclosure of which is incorporated by reference herein; U.S. Pub. No. 2012/0203247, entitled "Robotically-Controlled Surgical End Effector System," published Aug. 9, 2012, now U.S. Pat. No. 8,783,541, issued on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, now U.S. Pat. No. 8,479,969, issued on Jul. 9, 2013; U.S. Pub. No. 2012/0138660, entitled "Robotically-Controlled Cable-Based Surgical End Effectors," published Jun. 7, 2012, now U.S. Pat. No. 8,800,838, issued on Aug. 12, 2014, the disclosure of which is incorporated by reference herein; U.S. Pub. No. 2012/0205421, entitled "Robotically-Controlled Surgical End Effector System with Rotary Actuated Closure Systems," published Aug. 16, 2012, now U.S. Pat. No. 8,573,465, issued on Nov. 5, 2013, the disclosure of which is incorporated by reference herein; U.S. patent application Ser. No. 13/443,101, entitled "Control Interface for Laparoscopic Suturing Instrument," filed Apr. 10, 2012, published as U.S. Pub. No. 2013/0267969 on Oct. 10, 2013, the disclosure of which is incorporated by reference herein; and U.S. Provisional Pat. App. No. 61/597,603, entitled "Robotically Controlled Surgical Instrument," filed Feb. 10, 2012, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 12 depicts a left side elevational view of the instrument of FIG. 4, with the top cover removed;

FIG. 13 depicts a right side elevational view of the instrument of FIG. 4, with the top cover removed;

Figure 1:
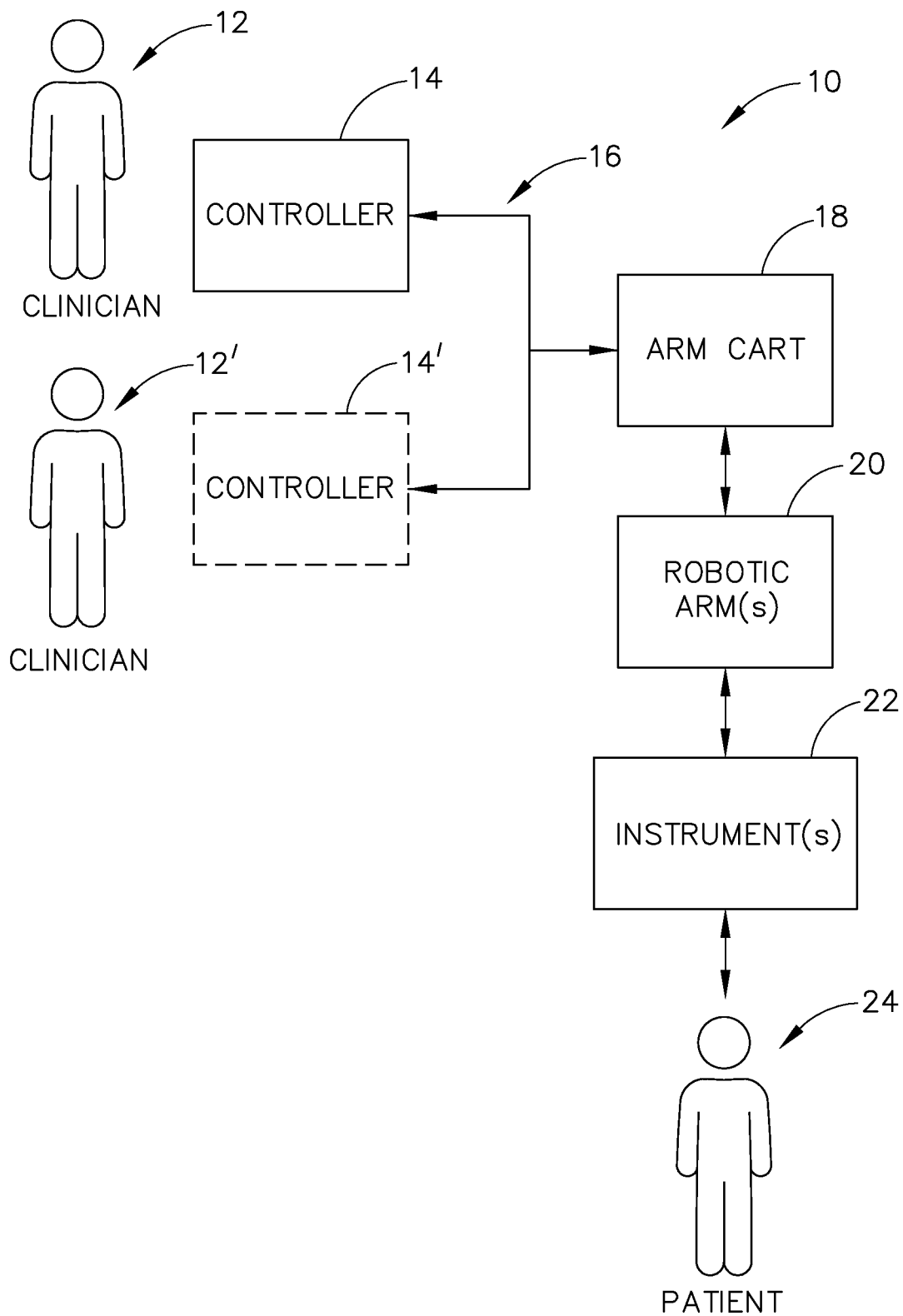
FIG. 1 depicts a block diagram of an exemplary robotic surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a robotic surgical driver comprising a proximal housing having an interface that mechanically and electrically couples with a surgical instrument having a distal surgical end effector. The term "proximal" refers the position of an element closer to the robotic surgical driver housing and the term "distal" refers to the position of an element closer to the surgical end effector of the surgical instrument and further away from the housing.

I. Exemplary Robotic Surgical System Overview

FIG. 1 illustrates an exemplary robotic surgical system (10). System (10) comprises at least one controller (14) and at least one arm cart (18). Arm cart (18) is mechanically and/or electrically coupled to one or more robotic manipulators or arms (20). Each robotic arm (20) comprises one or more surgical instruments (22) for performing various surgical tasks on a patient (24). Operation of arm cart (18), including arms (20) and instruments (22), may be directed by a clinician (12) from controller (14). In some examples, a second controller (14'), operated by a second clinician (12'), may also direct operation of the arm cart (18) in conjunction with the first clinician (12'). For example, each of the clinicians (12, 12') may control different arms (20) of the cart or, in some cases, complete control of arm cart (18) may be passed between the clinicians (12, 12'). In some examples, additional arm carts (not shown) may be utilized on the patient (24). These additional arm carts may be controlled by one or more of the controllers (14, 14').

Arm cart(s) (18) and controllers (14, 14') may be in communication with one another via a communications link (16), which may be any suitable type of wired and/or wireless communications link carrying any suitable type of signal (e.g., electrical, optical, infrared, etc.) according to any suitable communications protocol. Communications link (16) may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network.

Figure 2:
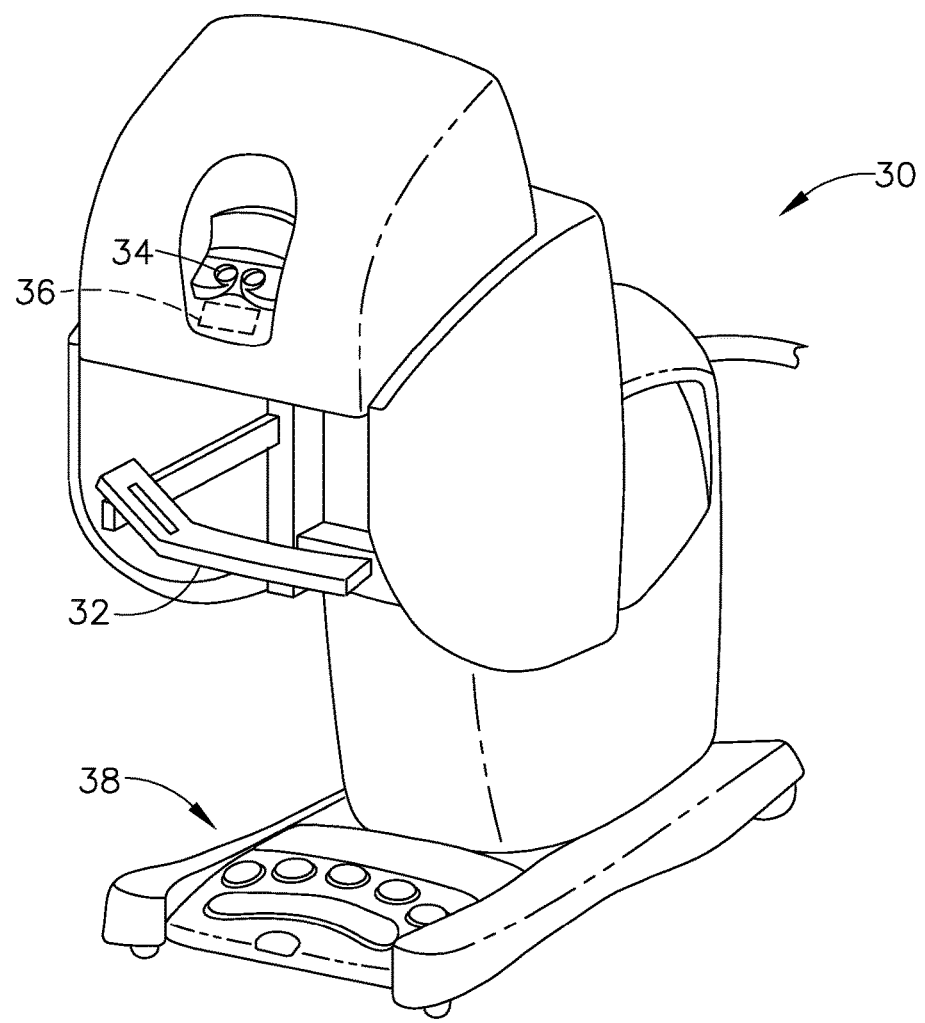
FIG. 2 depicts a perspective view of an exemplary controller of the system of FIG. 1.

FIG. 2 shows an exemplary controller (30) that may serve as a controller (14) of system (10). In this example, controller (30) generally includes user input assembly (32) having precision user input features (not shown) that are grasped by the surgeon and manipulated in space while the surgeon views the surgical procedure via a stereo display (34). The user input features of user input assembly (32) may include manual input devices that move with multiple degrees of freedom; and that include an actuatable handle for intuitively actuating tools (e.g., for closing grasping saws, applying an electrical potential to an electrode, etc). Controller (30) of the present example also includes an array of footswitches (38) providing additional control of arms (20) and instruments (22) to the surgeon. Display (34) may show views from one or more endoscopes viewing the surgical site within the patient and/or any other suitable view(s). In addition, a feedback meter (36) may be viewed through the display (34) and provide the surgeon with a visual indication of the amount of force being applied to a component of instrument (22) (e.g., a cutting member or clamping member, etc.). Other sensor arrangements may be employed to provide controller (30) with an indication as to whether a staple cartridge has been loaded into an end effector of instrument (22), whether an anvil of instrument (22) has been moved to a closed position prior to firing, and/or some other operational condition of instrument (22).

Figure 3:
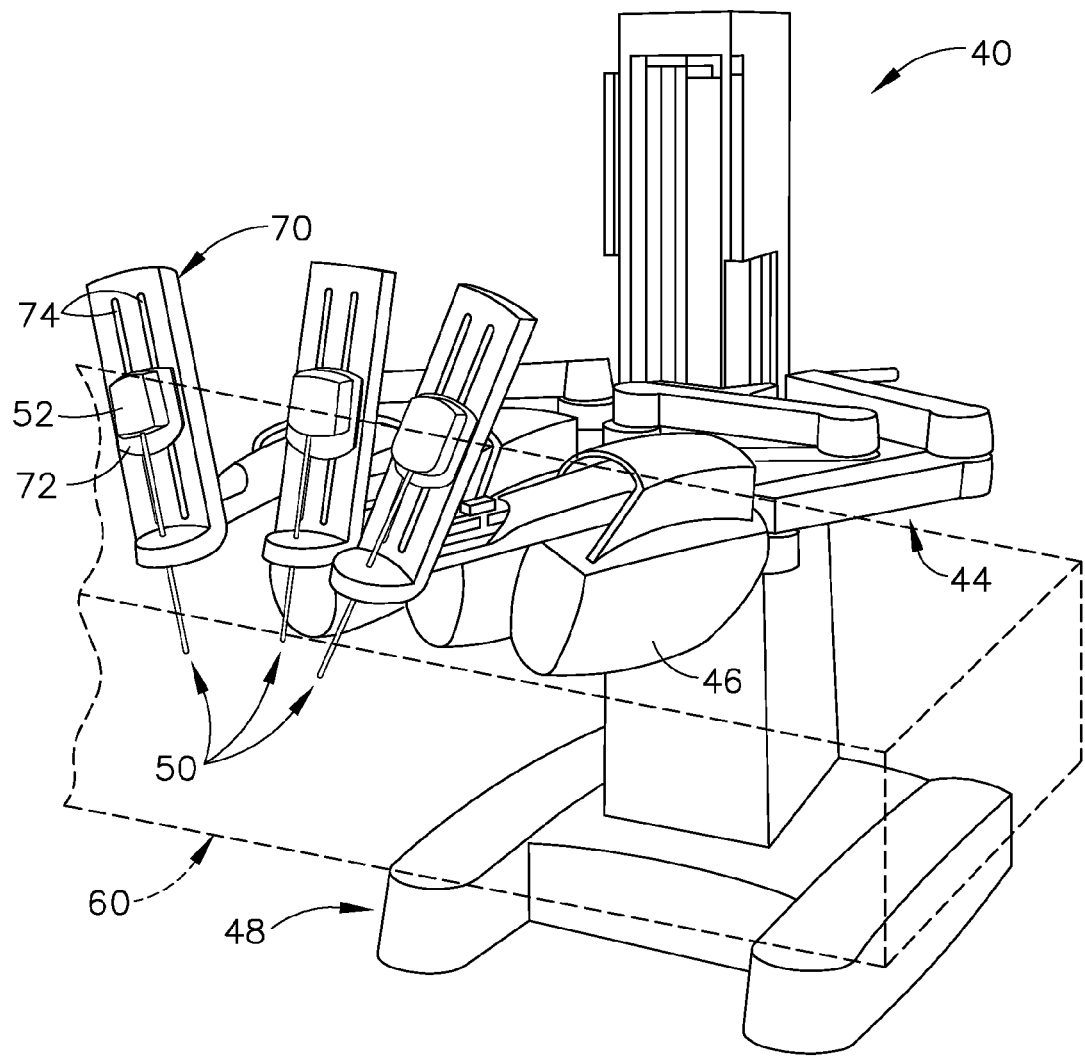
FIG. 3 depicts a perspective view of an exemplary robotic arm cart of the system of FIG. 1.
Figure 4:
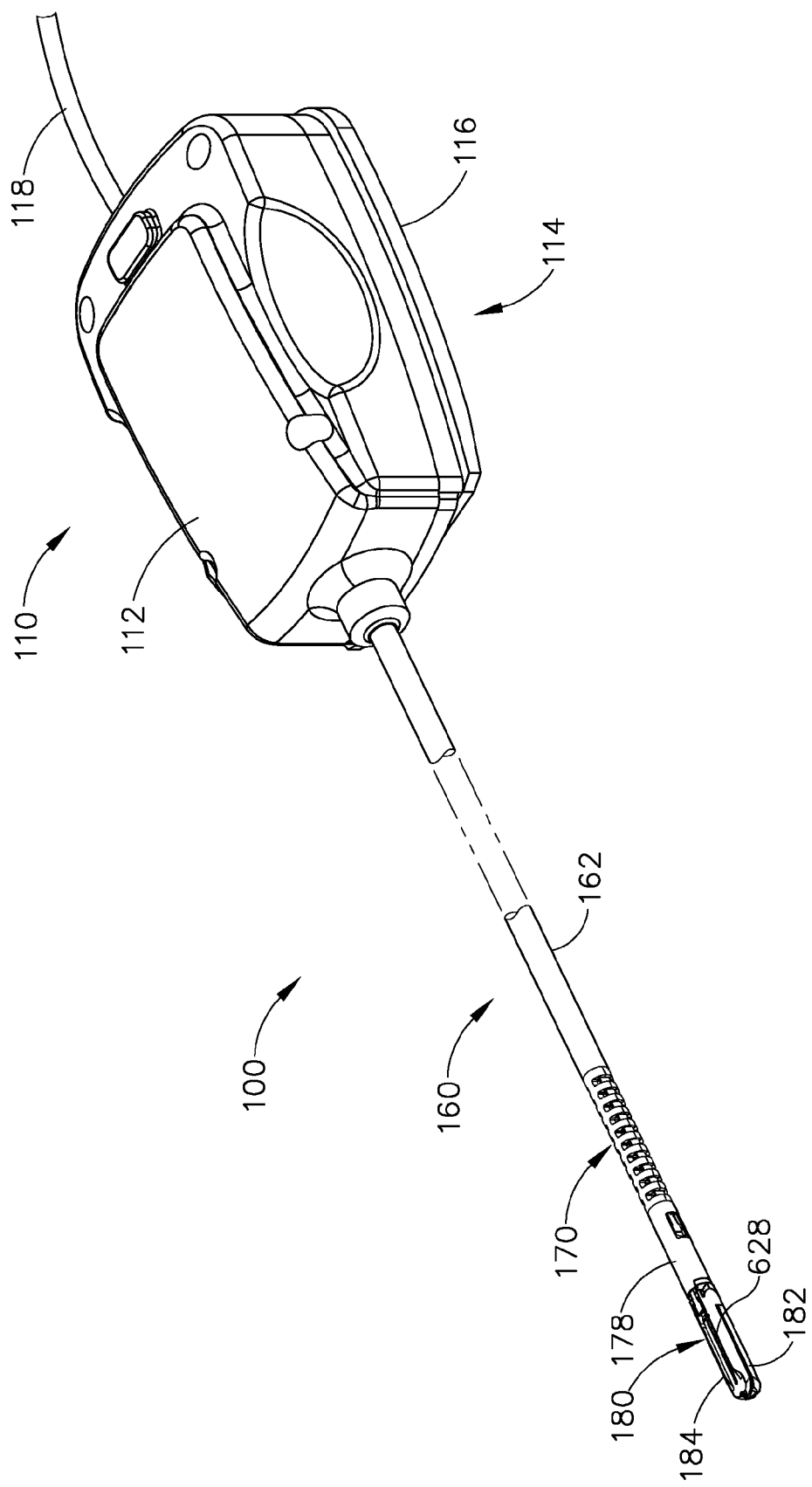
FIG. 4 depicts a perspective view of an exemplary surgical instrument suitable for incorporation with the system of FIG. 1.

FIG. 3 shows an exemplary robotic arm cart (40) that may serve as of arm cart (18) of system (10). In this example, arm cart (40) is operable to actuate a plurality of surgical instruments (50). While three instruments (50) are shown in this example, it should be understood that arm cart (40) may be operable to support and actuate any suitable number of surgical instruments (50). Surgical instruments (50) are each supported by a series of manually articulatable linkages, generally referred to as set-up joints (44), and a robotic manipulator (46). These structures are herein illustrated with protective covers extending over much of the robotic linkage. These protective covers may be optional, and may be limited in size or entirely eliminated in some versions to minimize the inertia that is encountered by the servo mechanisms used to manipulate such devices, to limit the volume of moving components so as to avoid collisions, and to limit the overall weight of cart (40).

Each robotic manipulator (46) terminates at an instrument platform (70), which is pivotable, rotatable, and otherwise movable by manipulator (46). Each platform includes an instrument dock (72) that is slidable along a pair of tracks (74) to further position instrument (50). Such sliding is motorized in the present example. Each instrument dock (72) includes mechanical and electrical interfaces that couple with an interface assembly (52) of instrument (50). By way of example only, dock (72) may include four rotary outputs that couple with complementary rotary inputs of interface assembly (52). Such rotary drive features may drive various functionalities in instrument (50), such as is described in various references cited herein and/or as is described in greater detail below. Electrical interfaces may establish communication via physical contact, inductive coupling, and/or otherwise; and may be operable to provide electrical power to one or more features in instrument (50), provide commands and/or data communication to instrument (50), and/or provide commands and/or data communication from instrument (50). Various suitable ways in which an instrument dock (72) may mechanically and electrically communicate with an interface assembly (52) of an instrument (50) will be apparent to those of ordinary skill in the art in view of the teachings herein. It should also be understood that instrument (50) may include one or more cables that couple with a separate power source and/or control unit, to provide communication of power and/or commands/data to/from instrument (50).

Arm cart (40) of the present example also includes a base (48) that is movable (e.g., by a single attendant) to selectively position arm cart (40) in relation to a patient. Cart (40) may generally have dimensions suitable for transporting the cart (40) between operating rooms. Cart (40) may be configured to fit through standard operating room doors and onto standard hospital elevators. In some versions, an automated instrument reloading system (not shown) may also be positioned in or near the work envelope (60) of arm cart (40), to selectively reload components (e.g., staple cartridges, etc.) of instruments (50).

In addition to the foregoing, it should be understood that one or more aspects of system (10) may be constructed in accordance with at least some of the teachings of U.S. Pat. No. 5,792,135; U.S. Pat. No. 5,817,084; U.S. Pat. No. 5,878,193; U.S. Pat. No. 6,231,565; U.S. Pat. No. 6,783,524; U.S. Pat. No. 6,364,888; U.S. Pat. No. 7,524,320; U.S. Pat. No. 7,691,098; U.S. Pat. No. 7,806,891; U.S. Pat. No. 7,824,401; and/or U.S. Pub. No. 2013/0012957, now U.S. Pat. No. 8,844,789, issued on Sep. 30, 2014. The disclosures of each of the foregoing U.S. patents and U.S. patent Publication are incorporated by reference herein. Still other suitable features and operabilities that may be incorporated into system (10) will be apparent to those of ordinary skill in the art in view of the teachings herein.

II. Exemplary Electrosurgical Instrument with Articulation Feature

FIGS. 4-13 show an exemplary electrosurgical instrument (100) that may be used as at least one instrument (50) within system (10). At least part of instrument (100) may be constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pub. No. 2011/0087218, now U.S. Pat. No. 8,939,974, issued on Jan. 27, 2015; U.S. Pub. No. 2012/0116379, now U.S. Pat. No. 9,161,803, issued on Oct. 20, 2015; U.S. Pub. No. 2012/0078243; U.S. Pub. No. 2012/0078247, now U.S. Pat. No. 9,402,682, issued on Aug. 2, 2016; U.S. Pub. No. 2013/0030428, now U.S. Pat. No. 9,089,327, issued on Jul. 28, 2015; and/or U.S. Pub. No. 2013/0023868, now U.S. Pat. No. 9,545,253, issued on Jan. 17, 2017. As described therein and as will be described in greater detail below, instrument (100) is operable to cut tissue and seal or weld tissue (e.g., a blood vessel, etc.) substantially simultaneously. In other words, instrument (100) operates similar to an endocutter type of stapler, except that instrument (100) provides tissue welding through application of bipolar RF energy instead of providing lines of staples to join tissue. It should also be understood that instrument (100) may have various structural and functional similarities with the ENSEAL® Tissue Sealing Device by Ethicon Endo-Surgery, Inc., of Cincinnati, Ohio. Furthermore, instrument (100) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to instrument (100), there is no intent for any of the description herein to be presumed as admitted prior art. Several teachings herein will in fact go beyond the scope of the teachings of the references cited herein and the ENSEAL® Tissue Sealing Device by Ethicon Endo-Surgery, Inc., of Cincinnati, Ohio.

Instrument (100) of the present example includes an interface assembly (110), a shaft assembly (160), an articulation section (170), and an end effector (180). Interface assembly (110) is configured to couple with a dock (72) of robotic arm cart (40) and is thereby further operable to drive articulation section (170) and end effector (180) as will be described in greater detail below. As will also be described in greater detail below, instrument (100) is operable to articulate end effector (180) to provide a desired positioning relative to tissue (e.g., a large blood vessel, etc.), then sever the tissue and apply bipolar RF energy to the tissue with end effector (180) to thereby seal the tissue.

A. Exemplary Shaft Assembly and Articulation Section

Figure 5:
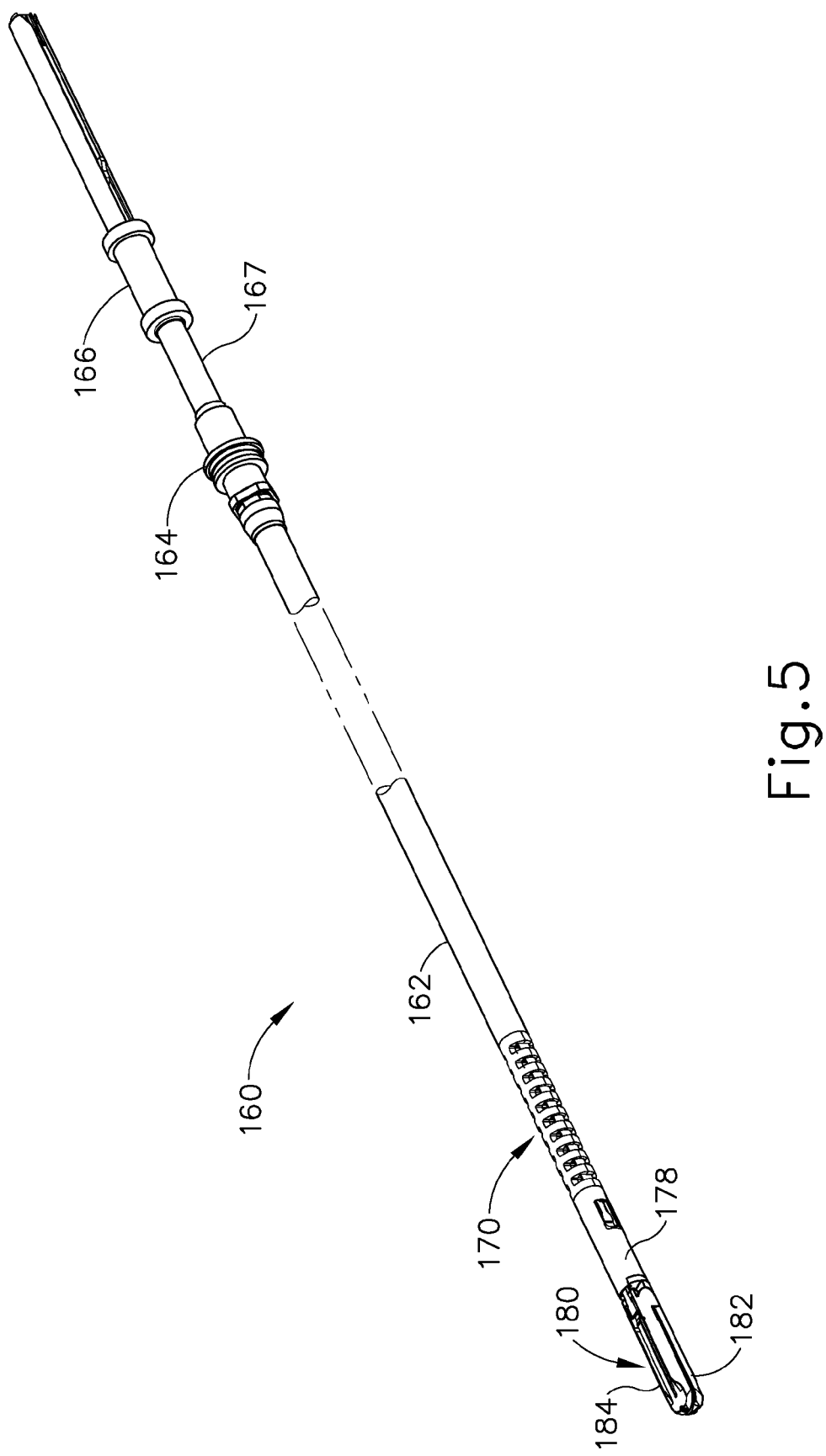
FIG. 5 depicts a perspective view of the shaft assembly of the surgical instrument of FIG. 4.

Shaft assembly (160) of the present example extends distally from interface assembly (110). Articulation section (170) is located at the distal end of shaft assembly (160), with end effector (180) being located distal to articulation section (170). Shaft assembly (160) includes an outer sheath (162) that encloses drive features and electrical features that couple interface assembly (110) with articulation section (170) and end effector (180). As best seen in FIG. 5, shaft assembly (160) further includes a unitary rotary coupling (164) and a firing beam coupling (166). Shaft assembly (160) is rotatable about the longitudinal axis defined by sheath (162), relative to interface assembly (110), via rotary coupling (164). Such rotation may provide rotation of end effector (180), articulation section (170), and shaft assembly (160) unitarily. In some other versions, rotary coupling (164) is operable to rotate end effector (180) without rotating any portion of shaft assembly (160) that is proximal of articulation section (170). As another merely illustrative example, instrument (100) may include one rotation control that provides rotatability of shaft assembly (160) and end effector (180) as a single unit; and another rotation control that provides rotatability of end effector (180) without rotating any portion of shaft assembly (160) that is proximal of articulation section (170). Other suitable rotation schemes will be apparent to those of ordinary skill in the art in view of the teachings herein. Of course, rotatable features may simply be omitted if desired.

Articulation section (170) is operable to selectively position end effector (180) at various angles relative to the longitudinal axis defined by sheath (162). Articulation section (170) may take a variety of forms. By way of example only, articulation section (170) may be configured in accordance with one or more teachings of U.S. Pub. No. 2012/0078247, now U.S. Pat. No. 9,402,682, issued on Aug. 2, 2016, the disclosure of which is incorporated by reference herein. As another merely illustrative example, articulation section (170) may be configured in accordance with one or more teachings of U.S. Pub. No. 2012/0078248, entitled "Articulation Joint Features for Articulating Surgical Device," published Mar. 29, 2012, now U.S. Pat. No. 9,220,559, issued on Dec. 29, 2015, the disclosure of which is incorporated by reference herein. Various other suitable forms that articulation section (170) may take will be apparent to those of ordinary skill in the art in view of the teachings herein. It should also be understood that some versions of instrument (10) may simply lack articulation section (170).

Figure 6:
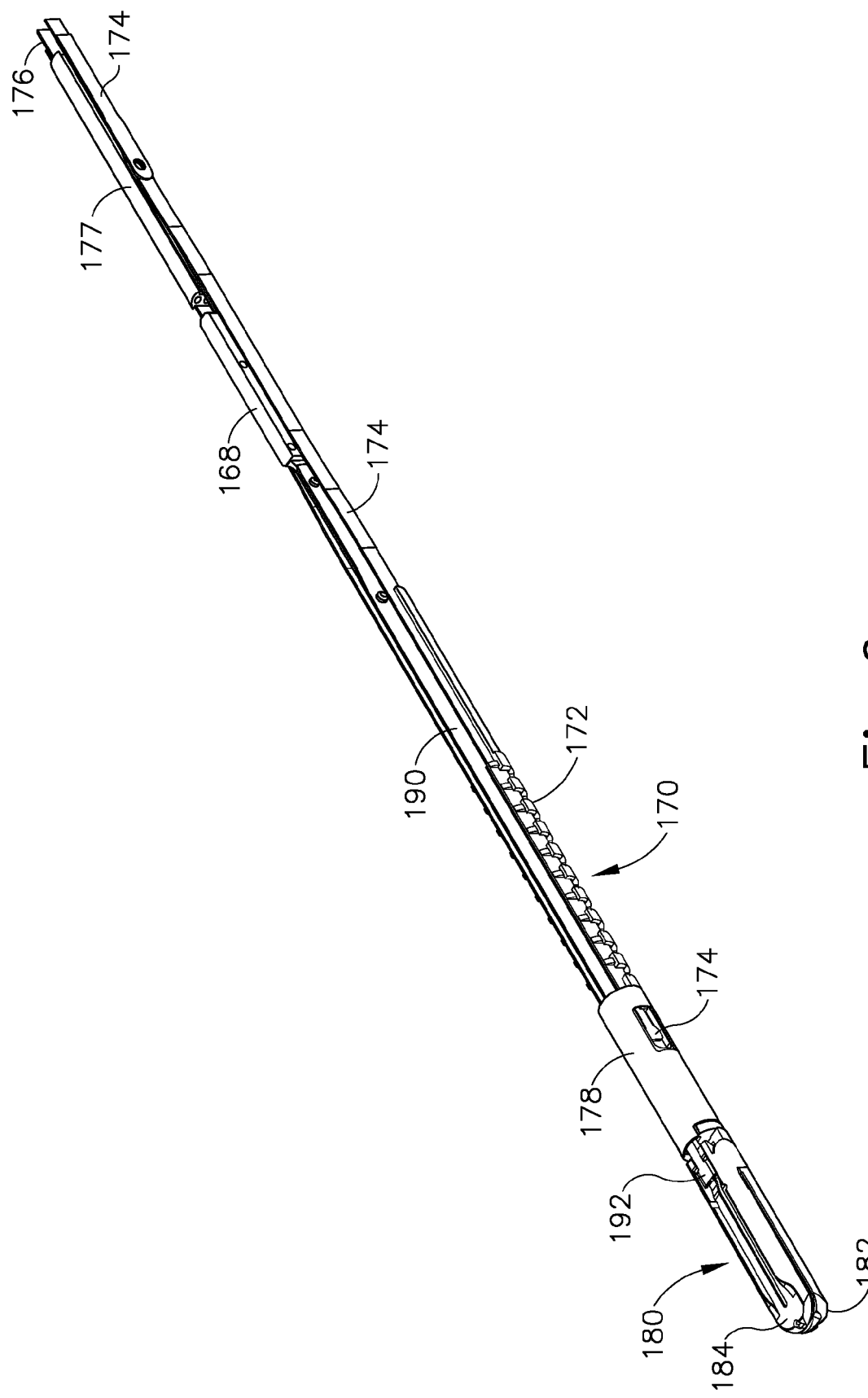
FIG. 6 depicts a perspective view of components of the shaft assembly of FIG. 5.
Figure 7:
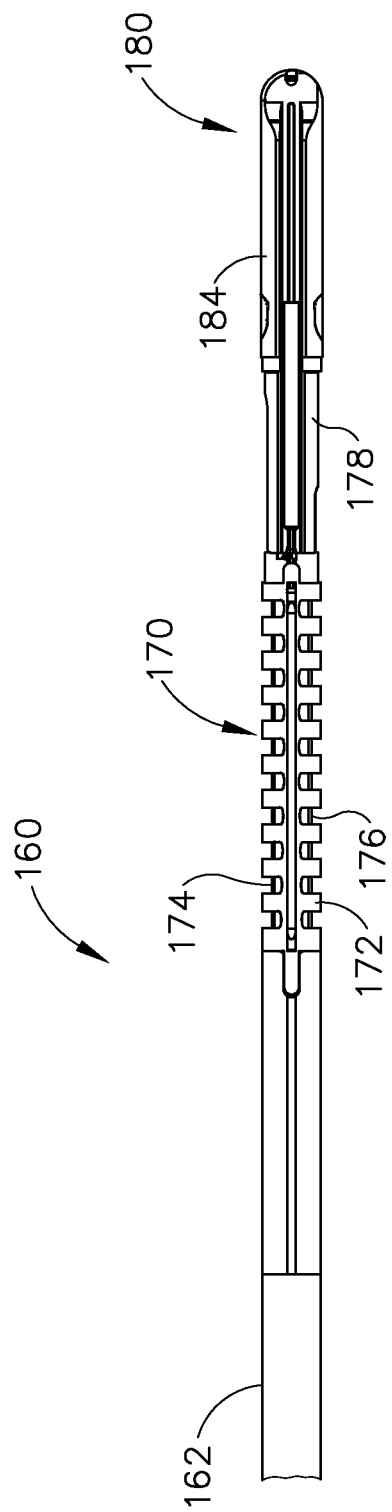
FIG. 7 depicts a top plan view of a distal portion of the shaft assembly of FIG. 5.

As best seen in FIGS. 6-7, articulation section (170) of the present example comprises a ribbed body (172) with a pair of articulation beams (174, 176) extending through ribbed body (172). An upper half of ribbed body (172) is omitted in FIG. 6. Articulation beams (174, 176) are distally anchored within a tube (178) that is positioned between end effector (180) and articulation section (170). Articulation beams (174, 176) are operable to articulate end effector (180) by laterally deflecting end effector (180) away from the longitudinal axis defined by sheath (162). In particular, and referring to the view shown in FIG. 7, end effector (180) will deflect toward articulation beam (174) when articulation beam (174) is retracted proximally while articulation beam (176) is advanced distally. End effector (180) will deflect toward articulation beam (176) when articulation beam (176) is retracted proximally while articulation beam (174) is advanced distally. Merely illustrative examples of how articulation beams (174, 176) may be opposingly translated will be described in greater detail below, while still other examples will be apparent to those of ordinary skill in the art in view of the teachings herein. As best seen in FIG. 6, a spacer body (177) is positioned between articulation beams (174, 176) and is operable to maintain beams (174, 176) in a substantially straight, separated relationship.

B. Exemplary End Effector

End effector (180) of the present example comprises a first jaw (182) and a second jaw (184). In the present example, first jaw (182) is substantially fixed relative to shaft assembly (160); while second jaw (184) pivots relative to shaft assembly (160), toward and away from first jaw (182). In some versions, actuators such as rods or cables, etc., may extend through sheath (162) and be joined with second jaw (184) at a pivotal coupling, such that longitudinal movement of the actuator rods/cables/etc. through shaft assembly (160) provides pivoting of second jaw (184) relative to shaft assembly (160) and relative to first jaw (182). Of course, jaws (182, 184) may instead have any other suitable kind of movement and may be actuated in any other suitable fashion. By way of example only, and as will be described in greater detail below, jaws (182, 184) may be actuated and thus closed by longitudinal translation of a firing beam (190), such that actuator rods/cables/etc. may simply be eliminated in some versions.

Figure 8:
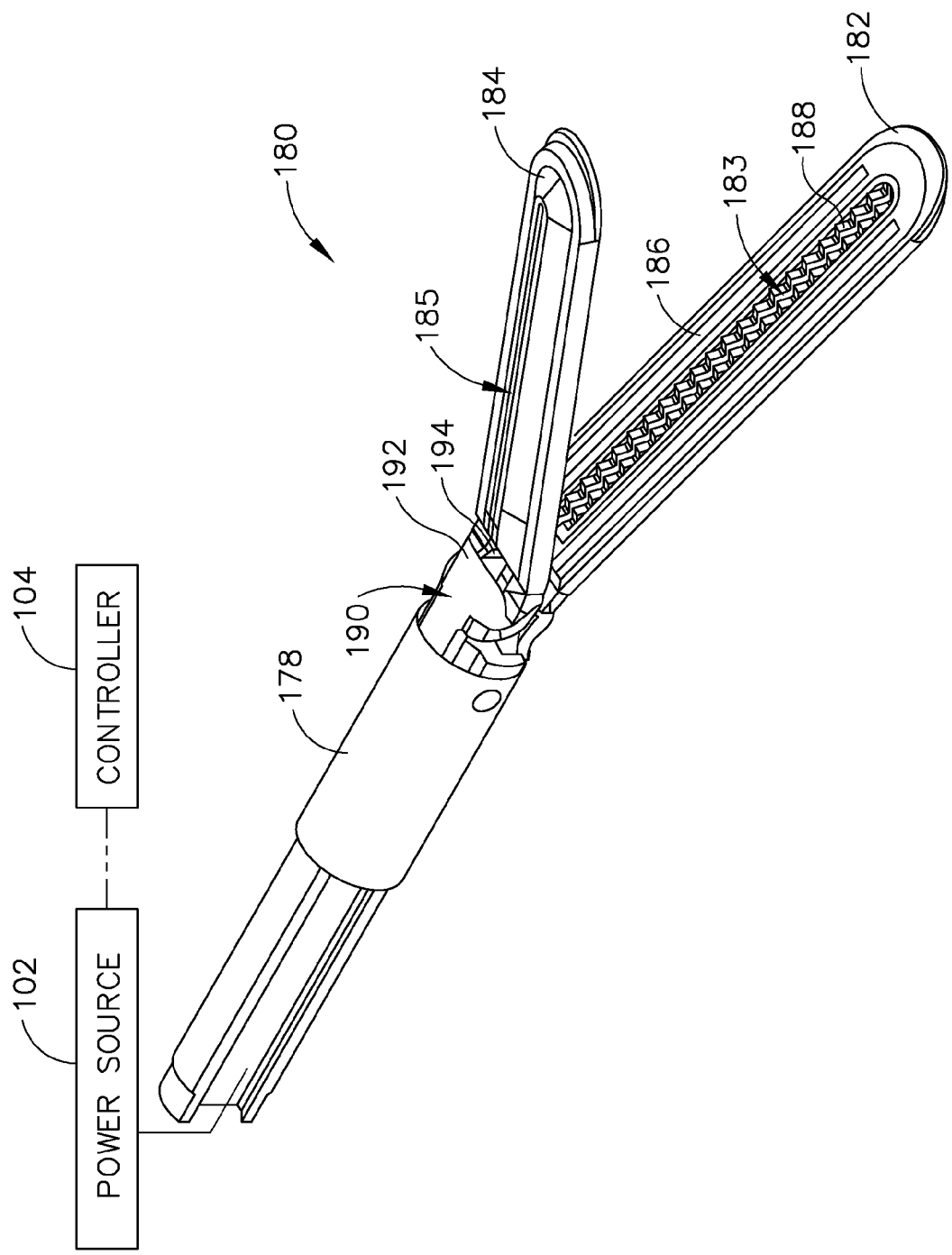
FIG. 8 depicts a perspective view of the end effector of the shaft assembly of FIG. 5, in an open configuration.
Figure 9:
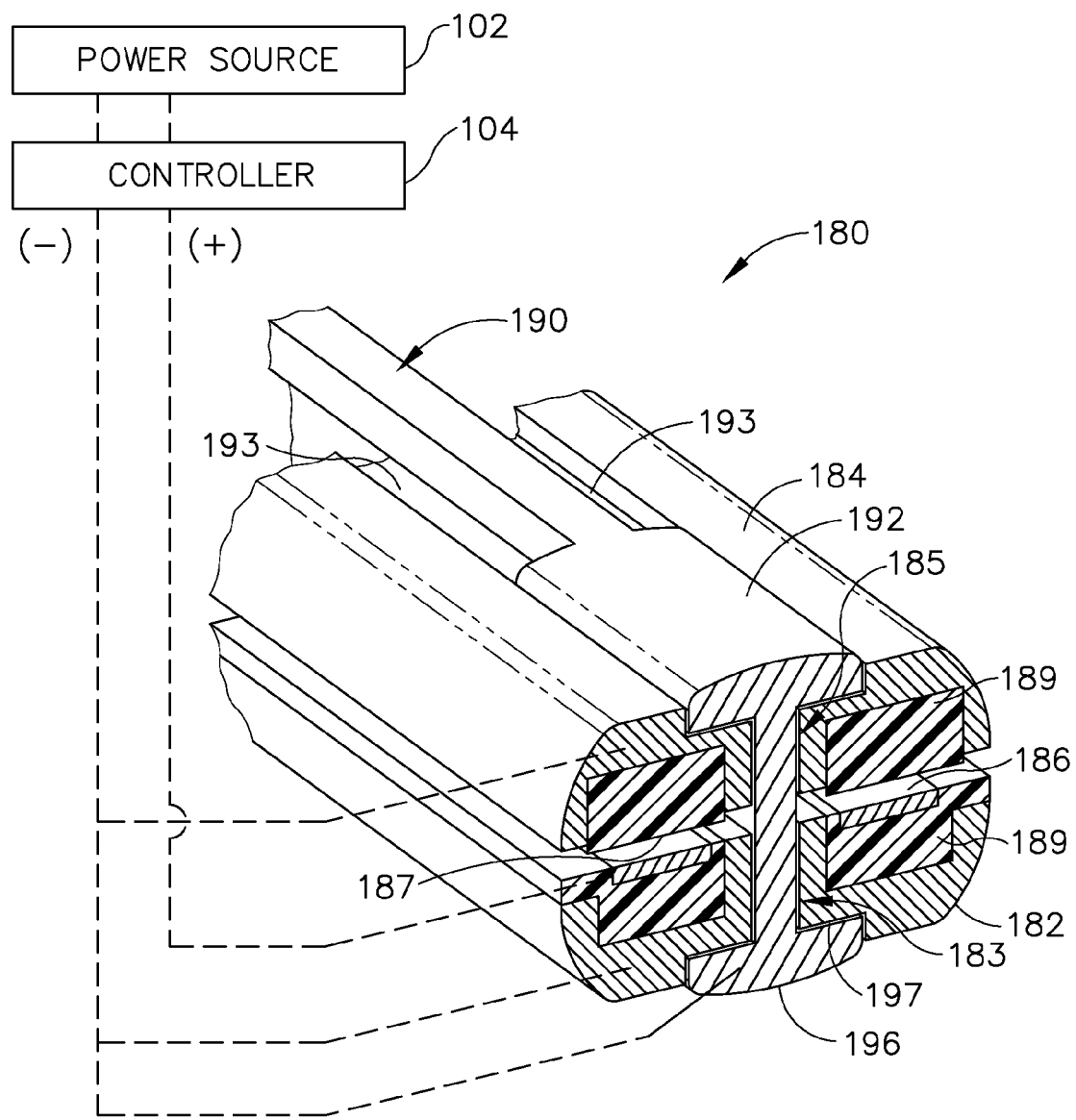
FIG. 9 depicts a perspective view in cross-section of the end effector of FIG. 8, taken along a lateral plane, with the end effector in a closed configuration.

As best seen in FIGS. 8-9, first jaw (182) defines a longitudinally extending elongate slot (183); while second jaw (184) also defines a longitudinally extending elongate slot (185). In addition, the top side of first jaw (182) presents a first electrode surface (186); while the underside of second jaw (184) presents a second electrode surface (187). Electrode surface (186, 187) are in communication with an electrical source (102) via one or more conductors (not shown) that extend along the length of shaft assembly (160). Electrical source (102) is operable to deliver RF energy to first electrode surface (186) at a first polarity and to second electrode surface (187) at a second (opposite) polarity, such that RF current flows between electrode surface (186, 187) and thereby through tissue captured between jaws (182, 184). In some versions, firing beam (190) serves as an electrical conductor that cooperates with electrode surface (186, 187) (e.g., as a ground return) for delivery of bipolar RF energy captured between jaws (182, 184).

Electrical source (102) may be external to instrument (100) or may be integral with instrument (100), as described in one or more references cited herein or otherwise. A controller (104) regulates delivery of power from electrical source (102) to electrode surfaces (186, 187). Controller (104) may also be external to instrument (100) or may be integral with electrosurgical instrument (100), as described in one or more references cited herein or otherwise. It should also be understood that electrode surfaces (186, 187) may be provided in a variety of alternative locations, configurations, and relationships. It should also be understood that power source (102) and/or controller (104) may be configured in accordance with at least some of the teachings of U.S. Provisional Pat. App. No. 61/550,768, entitled "Medical Instrument," filed Oct. 24, 2011, the disclosure of which is incorporated by reference herein; U.S. Pub. No. 2011/0082486, entitled "Devices and Techniques for Cutting and Coagulating Tissue," published Apr. 7, 2011, now U.S. Pat. No. 9,089,360, issued on Jul. 28, 2015, the disclosure of which is incorporated by reference herein; U.S. Pub. No. 2011/0087212, entitled "Surgical Generator for Ultrasonic and Electrosurgical Devices," published Apr. 14, 2011, now U.S. Pat. No. 8,986,302, issued on Mar. 24, 2015, the disclosure of which is incorporated by reference herein; U.S. Pub. No. 2011/0087213, entitled "Surgical Generator for Ultrasonic and Electrosurgical Devices," published Apr. 14, 2011, now U.S. Pat. No. 8,951,248, issued on Feb. 10, 2015, the disclosure of which is incorporated by reference herein; U.S. Pub. No. 2011/0087214, entitled "Surgical Generator for Ultrasonic and Electrosurgical Devices," published Apr. 14, 2011, now U.S. Pat. No. 9,039,695, issued on May 26, 2015, the disclosure of which is incorporated by reference herein; U.S. Pub. No. 2011/0087215, entitled "Surgical Generator for Ultrasonic and Electrosurgical Devices," published Apr. 14, 2011, now U.S. Pat. No. 9,050,093, issued on Jun. 9, 2015, the disclosure of which is incorporated by reference herein; U.S. Pub. No. 2011/0087216, entitled "Surgical Generator for Ultrasonic and Electrosurgical Devices," published Apr. 14, 2011, now U.S. Pat. No. 8,956,349, issued on Feb. 7, 2015, the disclosure of which is incorporated by reference herein; and/or U.S. Pub. No. 2011/0087217, entitled "Surgical Generator for Ultrasonic and Electrosurgical Devices," published Apr. 14, 2011, now U.S. Pat. No. 9,060,776, issued on Jun. 23, 2015, the disclosure of which is incorporated by reference herein. Other suitable configurations for power source (102) and controller (104) will be apparent to those of ordinary skill in the art in view of the teachings herein.

As best seen in FIG. 9, the lower side of first jaw (182) includes a longitudinally extending recess (197) adjacent to slot (183); while the upper side of second jaw (184) includes a longitudinally extending recess (193) adjacent to slot (185). FIG. 2 shows the upper side of first jaw (182) including a plurality of teeth serrations (188). It should be understood that the lower side of second jaw (184) may include complementary serrations that nest with serrations (188), to enhance gripping of tissue captured between jaws (182, 184) without necessarily tearing the tissue. Of course, serrations (188) may take any other suitable form or may be simply omitted altogether. It should also be understood that serrations (188) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (182, 184).

With jaws (182, 184) in a closed position, shaft assembly (160) and end effector (180) are sized and configured to fit through trocars having various inner diameters, such that instrument (100) is usable in minimally invasive surgery, though of course instrument (100) could also be used in open procedures if desired. By way of example only, with jaws (182, 184) in a closed position, shaft assembly (160) and end effector (180) may present an outer diameter of approximately 5 mm. Alternatively, shaft assembly (160) and end effector (180) may present any other suitable outer diameter (e.g., between approximately 2 mm and approximately 20 mm, etc.).

In some versions, end effector (180) includes one or more sensors (not shown) that are configured to sense a variety of parameters at end effector (180), including but not limited to temperature of adjacent tissue, electrical resistance or impedance of adjacent tissue, voltage across adjacent tissue, forces exerted on jaws (182, 184) by adjacent tissue, etc. By way of example only, end effector (180) may include one or more positive temperature coefficient (PTC) thermistor bodies (189) (e.g., PTC polymer, etc.), located adjacent to electrodes (186, 187) and/or elsewhere. Data from sensors may be communicated to controller (104). Controller (104) may process such data in a variety of ways. By way of example only, controller (104) may modulate or otherwise change the RF energy being delivered to electrode surface (186, 187), based at least in part on data acquired from one or more sensors at end effector (180). In addition or in the alternative, controller (104) may alert the user to one or more conditions via an audio and/or visual feedback device (e.g., speaker, lights, display screen, etc.), based at least in part on data acquired from one or more sensors at end effector (180). It should also be understood that some kinds of sensors need not necessarily be in communication with controller (104), and may simply provide a purely localized effect at end effector (180). For instance, PTC thermistor bodies (189) at end effector (180) may automatically reduce the energy delivery at electrode surface (186, 187) as the temperature of the tissue and/or end effector (180) increases, thereby reducing the likelihood of overheating. In some such versions, a PTC thermistor element is in series with power source (102) and electrode surface (186, 187); and the PTC thermistor provides an increased impedance (reducing flow of current) in response to temperatures exceeding a threshold. Furthermore, it should be understood that electrode surface (186, 187) may be used as sensors (e.g., to sense tissue impedance, etc.). Various kinds of sensors that may be incorporated into instrument (100) will be apparent to those of ordinary skill in the art in view of the teachings herein. Similarly various things that can be done with data from sensors, by controller (104) or otherwise, will be apparent to those of ordinary skill in the art in view of the teachings herein. Other suitable variations for end effector (180) will also be apparent to those of ordinary skill in the art in view of the teachings herein.

Firing beam (190) is longitudinally movable along part of the length of end effector (180). Firing beam (190) is coaxially positioned within shaft assembly (160), extends along part of the length of shaft assembly (160), and translates longitudinally within shaft assembly (160) (including articulation section (170) in the present example), though it should be understood that firing beam (190) and shaft assembly (160) may have any other suitable relationship. As shown in FIG. 6, firing beam (190) is secured to a firing block (168), such that firing beam (190) and firing block (168) translate unitarily together within sheath (162). Firing block (168) is secured to firing tube (167), which is best seen in FIG. 5. Firing block (168) and firing tube (167) translate unitarily together within sheath (162). Firing beam coupling (166) is secured to firing tube (167), such that translating firing beam coupling (166) will translate firing beam (190) through the above-described couplings.

Firing beam (190) includes a sharp distal blade (194), an upper flange (192), and a lower flange (196). As best seen in FIGS. 8-9, distal blade (194) extends through slots (183, 185) of jaws (182, 184), with upper flange (192) being located above jaw (184) in recess (59) and lower flange (196) being located below jaw (182) in recess (58). The configuration of distal blade (194) and flanges (62, 66) provides an "I-beam" type of cross section at the distal end of firing beam (190). While flanges (192, 196) extend longitudinally only along a small portion of the length of firing beam (190) in the present example, it should be understood that flanges (192, 196) may extend longitudinally along any suitable length of firing beam (190). In addition, while flanges (192, 196) are positioned along the exterior of jaws (182, 184), flanges (192, 196) may alternatively be disposed in corresponding slots formed within jaws (182, 184). For instance, each jaw (182, 184) may define a "T"-shaped slot, with parts of distal blade (194) being disposed in one vertical portion of each "T"-shaped slot and with flanges (192, 196) being disposed in the horizontal portions of the "T"-shaped slots. Various other suitable configurations and relationships will be apparent to those of ordinary skill in the art in view of the teachings herein.

Distal blade (194) is substantially sharp, such that distal blade (194) will readily sever tissue that is captured between jaws (182, 184). Distal blade (194) is also electrically grounded in the present example, providing a return path for RF energy as described elsewhere herein. In some other versions, distal blade (194) serves as an active electrode. In addition or in the alternative, distal blade (194) may be selectively energized with ultrasonic energy (e.g., harmonic vibrations at approximately 55.5 kHz, etc.).

The "I-beam" type of configuration of firing beam (190) provides closure of jaws (182, 184) as firing beam (190) is advanced distally. In particular, flange (192) urges jaw (184) pivotally toward jaw (182) as firing beam (190) is advanced from a proximal position to a distal position, by bearing against recess (193) formed in jaw (184). This closing effect on jaws (182, 184) by firing beam (190) may occur before distal blade (194) reaches tissue captured between jaws (182, 184). Such staging of encounters by firing beam (190) may reduce the force required to actuate firing beam (190) distally through a full firing stroke. In other words, in some such versions, firing beam (190) may have already overcome an initial resistance required to substantially close jaws (182, 184) on tissue before encountering resistance from severing the tissue captured between jaws (182, 184). Of course, any other suitable staging may be provided.

In the present example, flange (192) is configured to cam against a ramp feature at the proximal end of jaw (184) to open jaw (184) when firing beam (190) is retracted to a proximal position and to hold jaw (184) open when firing beam (190) remains at the proximal position. This camming capability may facilitate use of end effector (180) to separate layers of tissue, to perform blunt dissections, etc., by forcing jaws (182, 184) apart from a closed position. In some other versions, jaws (182, 184) are resiliently biased to an open position by a spring or other type of resilient feature. While jaws (182, 184) close or open as firing beam (190) is translated in the present example, it should be understood that other versions may provide independent movement of jaws (182, 184) and firing beam (190). By way of example only, one or more cables, rods, beams, or other features may extend through shaft assembly (160) to selectively actuate jaws (182, 184) independently of firing beam (190).

C. Exemplary Robotic Arm Interface Assembly

FIGS. 4 and 10-13 show interface assembly (110) of the present example in greater detail. As shown, interface assembly (110) comprises a housing (112), a base (114), and a cable (118). Housing (112) comprises a shell that simply encloses drive components. In some versions, housing (112) also includes an electronic circuit board, chip, and/or other feature that is configured to identify instrument (100). Such identification may be carried out through cable (118). Cable (118) is configured to couple with power source (102) and controller (104). A strain relief (119) is provided at the interface of cable (118) and housing (112). It should be noted that housing (112) is omitted from FIGS. 11-13 for the sake of clarity.

Figure 10:
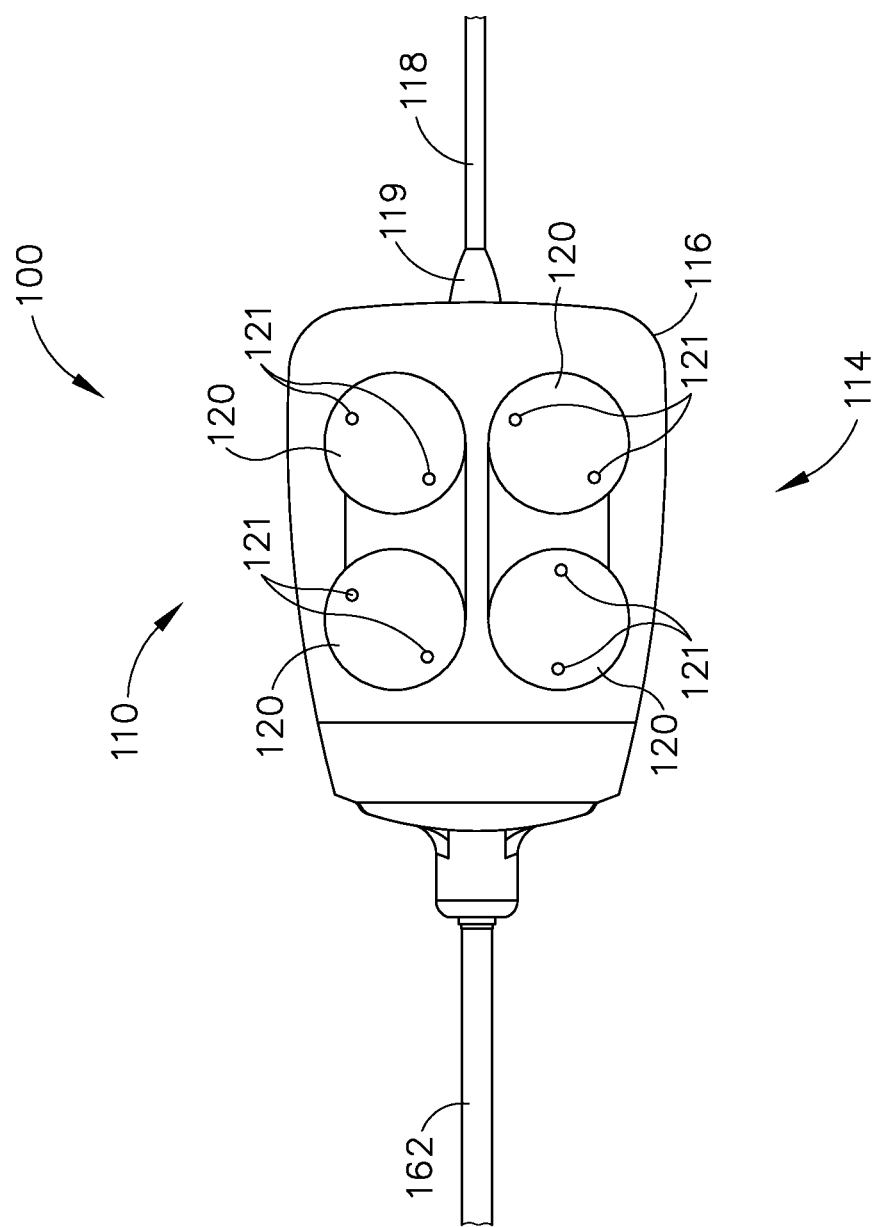
FIG. 10 depicts a bottom plan view of a proximal portion of the instrument of FIG. 4.
Figure 11:
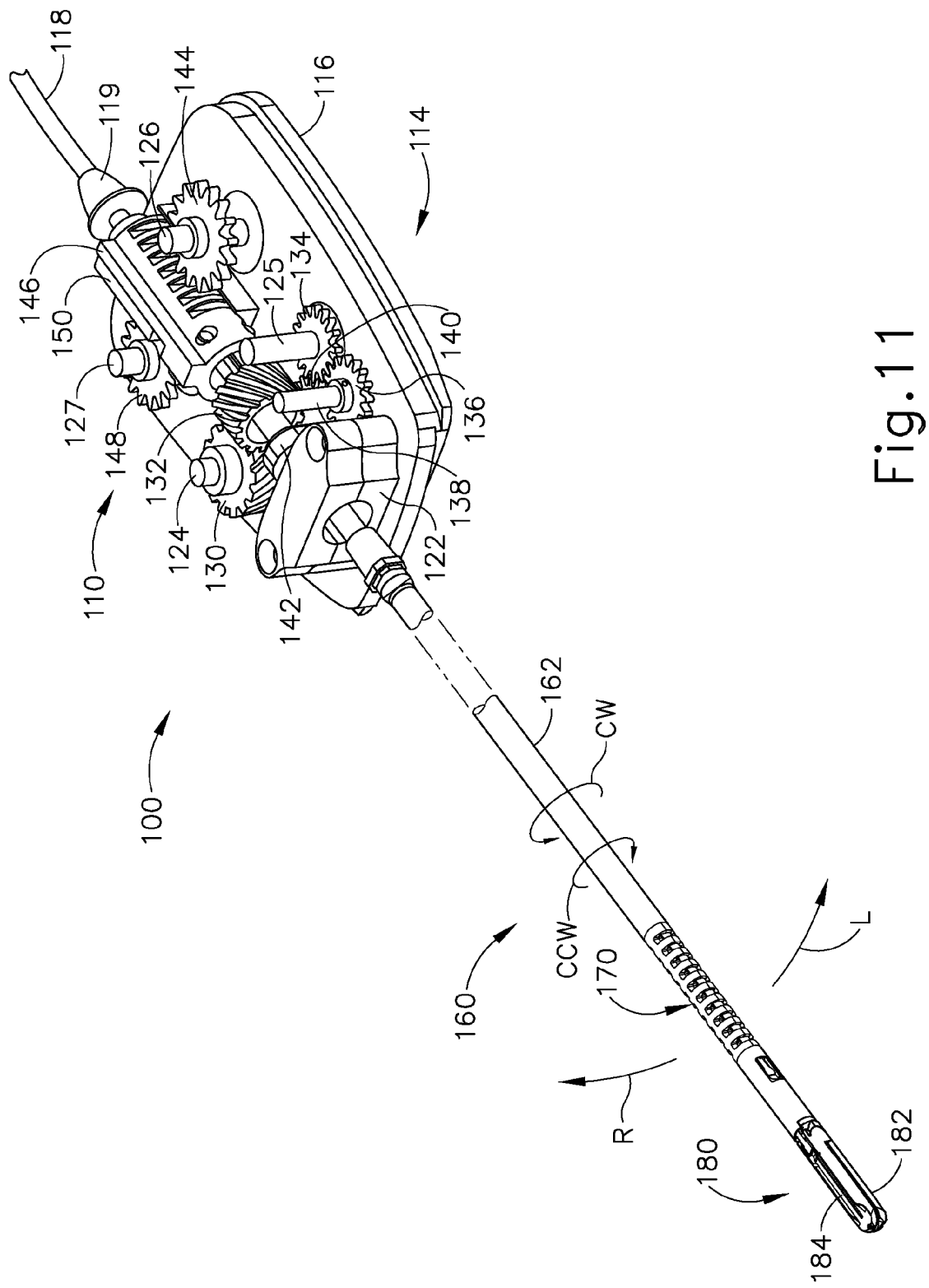
FIG. 11 depicts a perspective view of the instrument of FIG. 4, with a top cover removed.

Base (114) includes a mounting plate (116) that engages dock (72) of robotic arm cart (40). It should be noted that plate (116) is omitted from FIGS. 12-13 for the sake of clarity. While not shown, it should be understood that base (114) may also include one or more electrical contacts and/or other features operable to establish electrical communication with a complementary feature of dock (72). A shaft support structure (122) extends upwardly from base (114) and provides support to shaft assembly (160) (while still allowing shaft assembly (160) to rotate). By way of example only, shaft support structure (122) may include a busing, bearings, and/or other features that facilitate rotation of shaft assembly (160) relative to support structure (122). As shown in FIG. 10, base (114) further includes four drive discs (120) that are rotatable relative to plate (116). Each disc (120) includes a pair of unitary pins (121) that couple with complementary recesses (not shown) in drive elements of dock (72). In some versions, one pin (121) of each pair is closer to the axis of rotation of the corresponding disc (120), to ensure proper angular orientation of disc (120) relative to the corresponding drive element of dock (72). As best seen in FIGS. 11-13, a drive shaft (124, 125, 126, 127) extends unitarily upwardly from each disc (120). As will be described in greater detail below, discs (120) are operable to provide independent rotation of shaft assembly (160), bending of articulation section (170), and translation of firing beam (190), through rotation of drive shafts (124, 125, 126, 127).

As best seen in FIG. 11, a first helical gear (130) is fixedly secured to drive shaft (124), such that rotation of the corresponding disc (120) provides rotation of first helical gear (130). First helical gear (130) meshes with a second helical gear (132), which is fixedly secured to rotary coupling (164). Thus, rotation of first helical gear (130) provides rotation of shaft assembly (160). It should be understood that rotation of first helical gear (130) about a first axis is converted into rotation of second helical gear (132) about a second axis, which is orthogonal to the first axis. A clockwise (CW) rotation of second helical gear (132) results in CW rotation of shaft assembly (160). A counter-clockwise (CCW) rotation of second helical gear (132) results in CCW rotation of shaft assembly (160). Other suitable ways in which shaft assembly (160) may be rotated will be apparent to those of ordinary skill in the art in view of the teachings herein.

As best seen in FIGS. 11-12, a spur gear (134) is fixedly secured to drive shaft (125), such that rotation of the corresponding disc (120) provides rotation of spur gear (134). Spur gear (134) meshes with a first spur pinion (136), which is fixedly secured to a pinion shaft (138). Pinion shaft (138) is supported by base (116) and rotates freely relative to base (116), such that first spur pinion (136) is rotatable as an idler. It should therefore be understood that first spur pinion (136) rotates in response to rotation of spur gear (134). First spur pinion (136) also meshes with a rack (140), which is fixedly secured to a drive block (142). Drive block (142) is secured to firing beam coupling (166). Thus, rotation of first spur pinion (136) is converted to translation of firing beam (190) via rack (140), drive block (142), and firing beam coupling (166). As noted above, firing beam (190) is operable to first close jaws (182, 184) together about tissue during a first range of distal travel of firing beam (190); then sever the tissue clamped between jaws (182, 184) during a first range of distal travel of firing beam (190). Thus tissue may be clamped and severed by rotation of drive shaft (125) via its corresponding disc (120). When this rotation is reversed, firing beam (190) retracts proximally, ultimately opening jaws (182, 184) to release tissue. Other suitable ways in which firing beam (190) may be translated will be apparent to those of ordinary skill in the art in view of the teachings herein.

With respect to articulation control, FIGS. 11-12 show a second spur pinion (144) fixedly secured to drive shaft (126), such that rotation of the corresponding disc (120) provides rotation of second spur pinion (144). Second spur pinion (144) meshes with a left rack (146), which is fixedly secured to articulation beam (174). It should be understood that articulation beam (174) will translate distally or proximally in response to rotation of drive shaft (126). Similarly, FIGS. 11 and 13 show a third spur pinion (148) fixedly secured to drive shaft (127), such that rotation of the corresponding disc (120) provides rotation of third spur pinion (148). Third spur pinion (148) meshes with a right rack (150), which is fixedly secured to articulation beam (176). It should be understood that articulation beam (176) will translate distally or proximally in response to rotation of drive shaft (127).

It should also be understood that drive shafts (126, 127) may be rotated in the same direction simultaneously in order to provide opposing translation of beams (174, 176). For instance, drive shaft (126) may be rotated clockwise to retract beam (174) proximally, with drive shaft (127) being rotated clockwise to advance beam (176) distally, to thereby deflect end effector (180) to the left (L) at articulation section (170). Conversely, drive shaft (126) may be rotated counter-clockwise to advance beam (174) distally, with drive shaft (127) being rotated counter-clockwise to retract beam (176) proximally, to deflect end effector (180) to the left (R) at articulation section (170). Other suitable ways in which end effector (180) may be articulated at articulation section (170) will be apparent to those of ordinary skill in the art in view of the teachings herein. By way of example only, articulation control may be provided in accordance with at least some of the teachings of U.S. Pub. No. 2012/0078243, the disclosure of which is incorporated by reference herein; and/or U.S. Pub. No. 2013/0023868, now U.S. Pat. No. 9,545,253, issued on Jan. 17, 2017, the disclosure of which is incorporated by reference herein. It should also be understood that some versions of instrument (100) may simply lack an articulation section (170) and corresponding control.

D. Exemplary Operation

In an exemplary use, arm cart (40) is used to insert end effector (180) into a patient via a trocar. Articulation section (170) is substantially straight when end effector (180) and part of shaft assembly (160) are inserted through the trocar. Drive shaft (124) may be rotated through drive features in dock (72) that are coupled with the corresponding disc (120), to position end effector (180) at a desired angular orientation relative to the tissue. Drive shafts (126, 126) may then be rotated through drive features in dock (72) that are coupled with the corresponding discs (120), to pivot or flex articulation section (170) of shaft assembly (160) in order to position end effector (180) at a desired position and orientation relative to an anatomical structure within the patient. Two layers of tissue of the anatomical structure are then captured between jaws (182, 184) by rotating drive shaft (125) to advance firing beam (190) distally through a first range of motion. Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of instrument (100) is perpendicular to the longitudinal axis defined by end effector (180), etc.). In other words, the lengths of jaws (182, 184) may be oriented perpendicular to (or at least generally transverse to) the length of the blood vessel. As noted above, flanges (192, 196) cammingly act to pivot jaw (182) toward jaw (184) when firing beam (190) is actuated distally by rotating drive shaft (125).

With tissue layers captured between jaws (182, 184) firing beam (190) continues to advance distally in response to continued rotation of drive shaft (125). As firing beam (190) continues to advance distally, distal blade (194) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (192, 196) immediately above and below jaws (182, 184), respectively, may help keep jaws (182, 184) in a closed and tightly clamping position. In particular, flanges (192, 196) may help maintain a significantly compressive force between jaws (182, 184). With severed tissue layer portions being compressed between jaws (182, 184), electrode surfaces (186, 187) are activated with bipolar RF energy by the surgeon providing a corresponding command input through controller (30) (e.g., through user input assembly (32) or footswitches (38), etc.). In some versions, electrodes (186, 187) are selectively coupled with power source (102) such that electrode surface (186, 187) of jaws (182, 184) are activated with a common first polarity while firing beam (190) is activated at a second polarity that is opposite to the first polarity. Thus, a bipolar RF current flows between firing beam (190) and electrode surfaces (186, 187) of jaws (182, 184), through the compressed regions of severed tissue layer portions. In some other versions, electrode surface (186) has one polarity while electrode surface (187) and firing beam (190) both have the other polarity. In either version (among at least some others), bipolar RF energy delivered by power source (102) ultimately thermally welds the tissue layer portions on one side of firing beam (190) together and the tissue layer portions on the other side of firing beam (190) together.

In certain circumstances, the heat generated by activated electrode surfaces (186, 187) can denature the collagen within the tissue layer portions and, in cooperation with clamping pressure provided by jaws (182, 184), the denatured collagen can form a seal within the tissue layer portions. Thus, the severed ends of the natural lumen defining anatomical structure are hemostatically sealed shut, such that the severed ends will not leak bodily fluids. In some versions, electrode surface (186, 187) may be activated with bipolar RF energy before firing beam (190) even begins to translate distally and thus before the tissue is even severed. Other suitable ways in which instrument (100) may be operable and operated will be apparent to those of ordinary skill in the art in view of the teachings herein.

Figure 14:
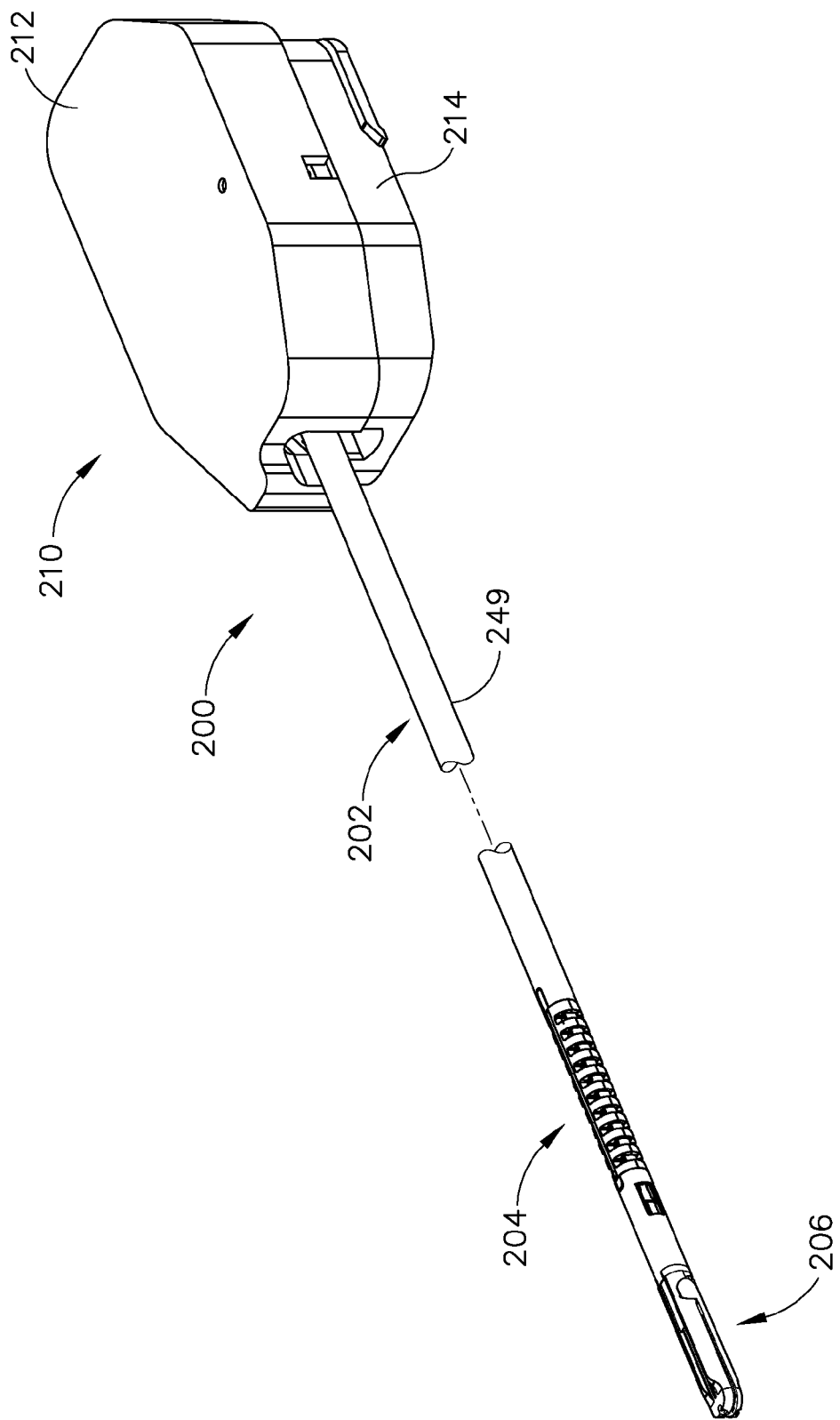
FIG. 14 depicts a top, perspective view of an exemplary alternative surgical instrument for incorporation with the system of FIG. 1.

III. Exemplary Alternative Electrosurgical Instrument with Articulation Feature and Rack Driven Components FIG. 14 shows an exemplary alternative electrosurgical instrument (200). Instrument (200) of this example is substantially similar to instrument (100) described above in that instrument (200) has a shaft assembly (202), an articulation section (204), and an end effector (206) that are substantially identical to shaft assembly (160), articulation section (170), and end effector (180) described above. Instrument (200) of this example is also operable to couple with a dock (72) of robotic arm cart (40) via an interface assembly (210). However, interface assembly (210) of this example is different from interface assembly (110) described above.

Figure 15:
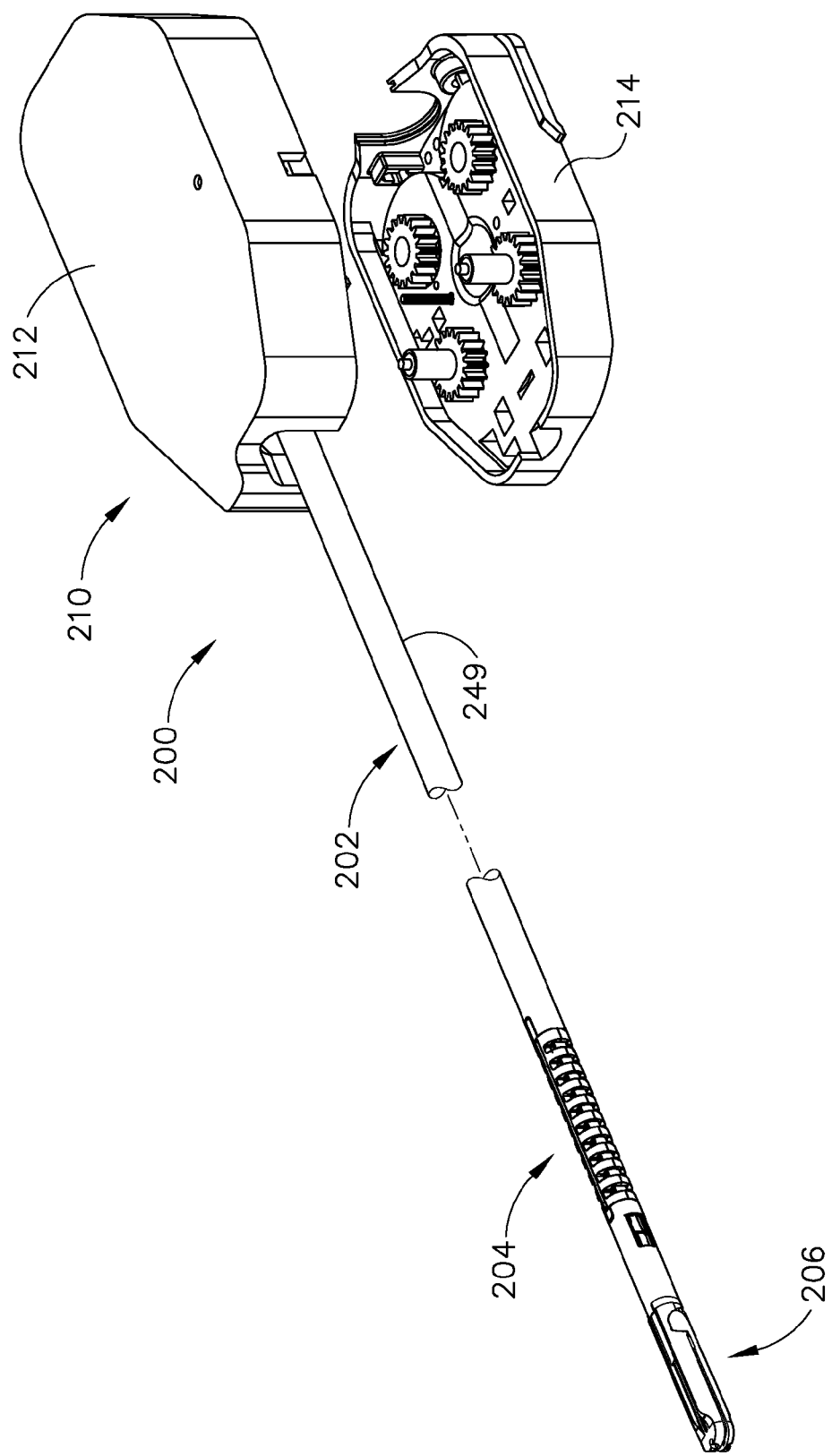
FIG. 15 depicts a top, perspective view of the surgical instrument of FIG. 14 with the cover removed from the base.

Interface assembly (210) comprises a housing (212) operable to house the various components further discussed below. Housing (212) has an upper clamshell structure operable to close upon a base (214) such that shaft assembly (202) extends from housing (212). FIG. 15 shows housing (212) removed from base (214). As seen in the illustrated version, shaft assembly (202) is connected to housing (212), though other variations will be described in further detail below. Housing (212) is operable to snap against base (214) though it will be understood that any suitable means for attaching housing (212) to base (214) may be used as would be apparent to one of ordinary skill in the art. As seen in FIG.

15, housing (212) is removable from base (214). It will be understood that during operation, housing (212) is snapped against base (214). When snapped against base (214), components in housing (212) engage components in base (214), which will be discussed in further detail below. Since housing (212) is separable from base (214), it will appreciated that housing (212) and components therein may be, in some cases, disposable after one or more uses, whereas base (214) remains as a reusable component, though it will be appreciated that other suitable configurations may be used as would be apparent to one of ordinary skill in the art in view of the teachings herein.

Figure 16:
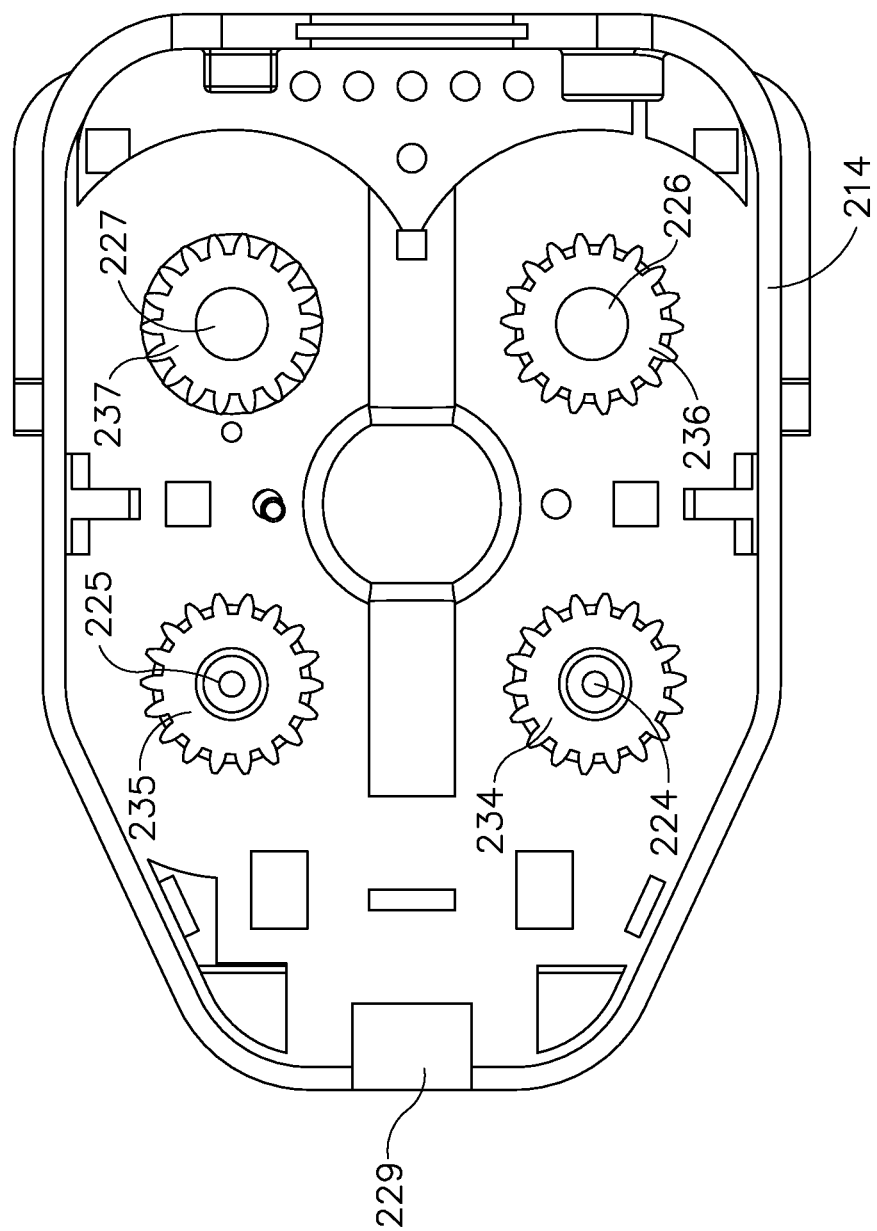
FIG. 16 depicts a top, plan view of the base of an interface assembly of the surgical instrument of FIG. 14.
Figure 20:
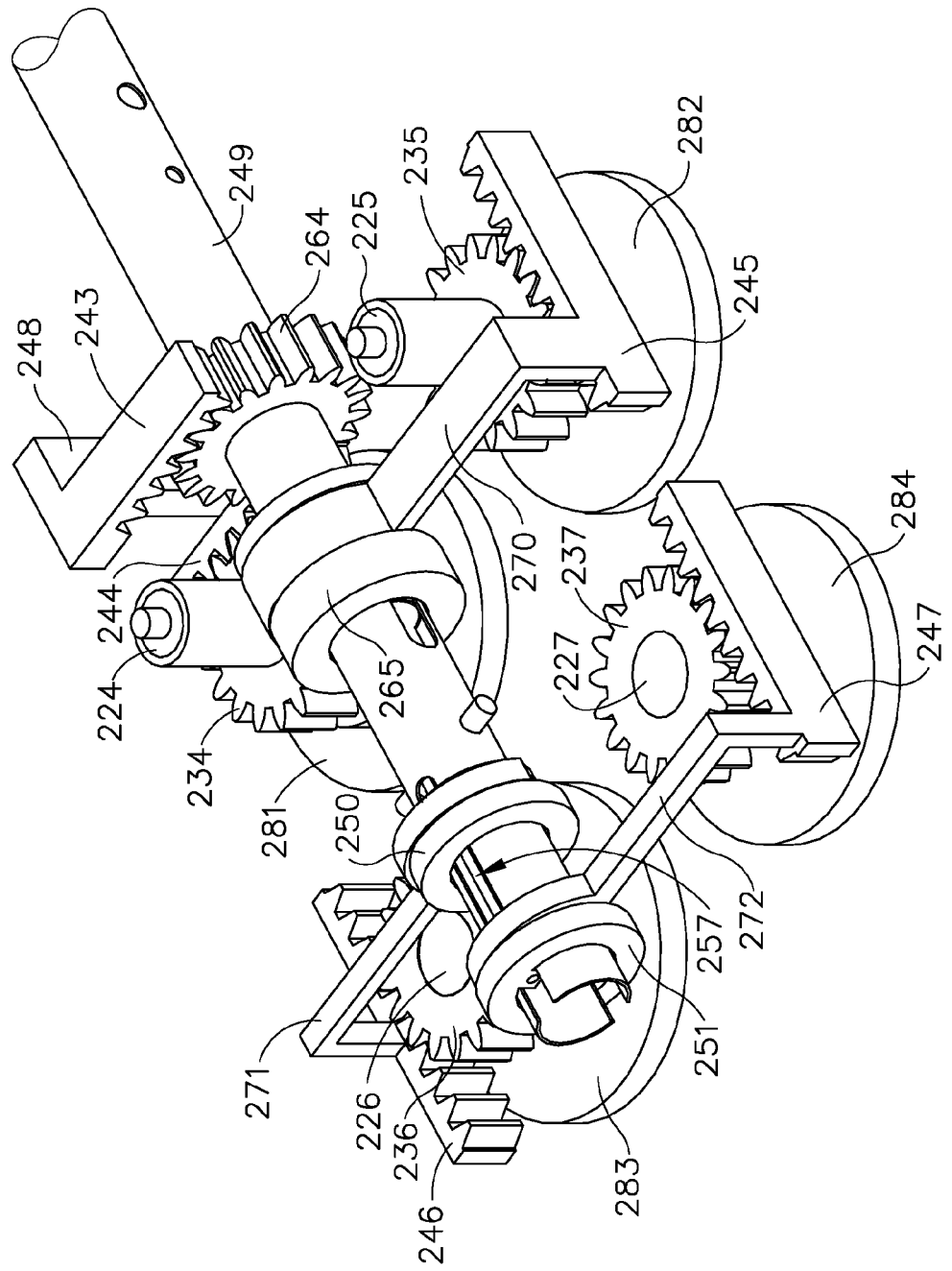
FIG. 20 depicts a rear, perspective, internal view of the drive components of FIG. 19.

FIG. 16 shows a top view of base (214). Base (214) comprises a first drive shaft (224), a second drive shaft (225), a third drive shaft (226), and a fourth drive shaft (227). Drive shafts (224, 225, 226, 227) are operable to engage instrument dock (72) of FIG. 3. Furthermore instrument dock (72) is configured to independently rotate drive shafts (224, 225, 226, 227). As shown in FIG. 20, drive shafts (224, 225, 226, 227) are secured to respective drive discs (281, 282, 283), which are substantially similar to drive discs (120) shown in FIG. 10 and described above. Drive discs (281, 282, 283) may thus be controlled through instrument dock (72) by a user to rotate drive shafts (224, 225, 226, 227). In other versions, instrument dock (72) may be operable to unitarily rotate any combinations of drive shafts (224, 225, 226, 227).

Drive shafts (224, 225, 226, 227) of the present example are positioned perpendicularly in relation to shaft assembly (202). In particular, shaft assembly (202) defines a longitudinal axis, and drive shafts (224, 225, 226, 227) extend upwardly and are positioned perpendicular in relation to the longitudinal axis defined by shaft assembly (202). However, it will be understood that drive shafts (224, 225, 226, 227) may be oriented in other ways in relation to shaft assembly (202). First drive shaft (224) is in communication with a first spur gear (234). When first drive shaft (224) rotates, first spur gear (234) also rotates. Second drive shaft (225) is in communication with a second spur gear (235). Similarly, when second drive shaft (225) rotates, second spur gear (235) also rotates. Third drive shaft (226) is in communication with third spur gear (236). When third drive shaft (226) rotates, third spur gear (236) also rotates. Finally, fourth drive shaft (227) is in communication with fourth spur gear (237) such that when fourth drive shaft (227) rotates, fourth spur gear (237) also rotates.

Figure 17:
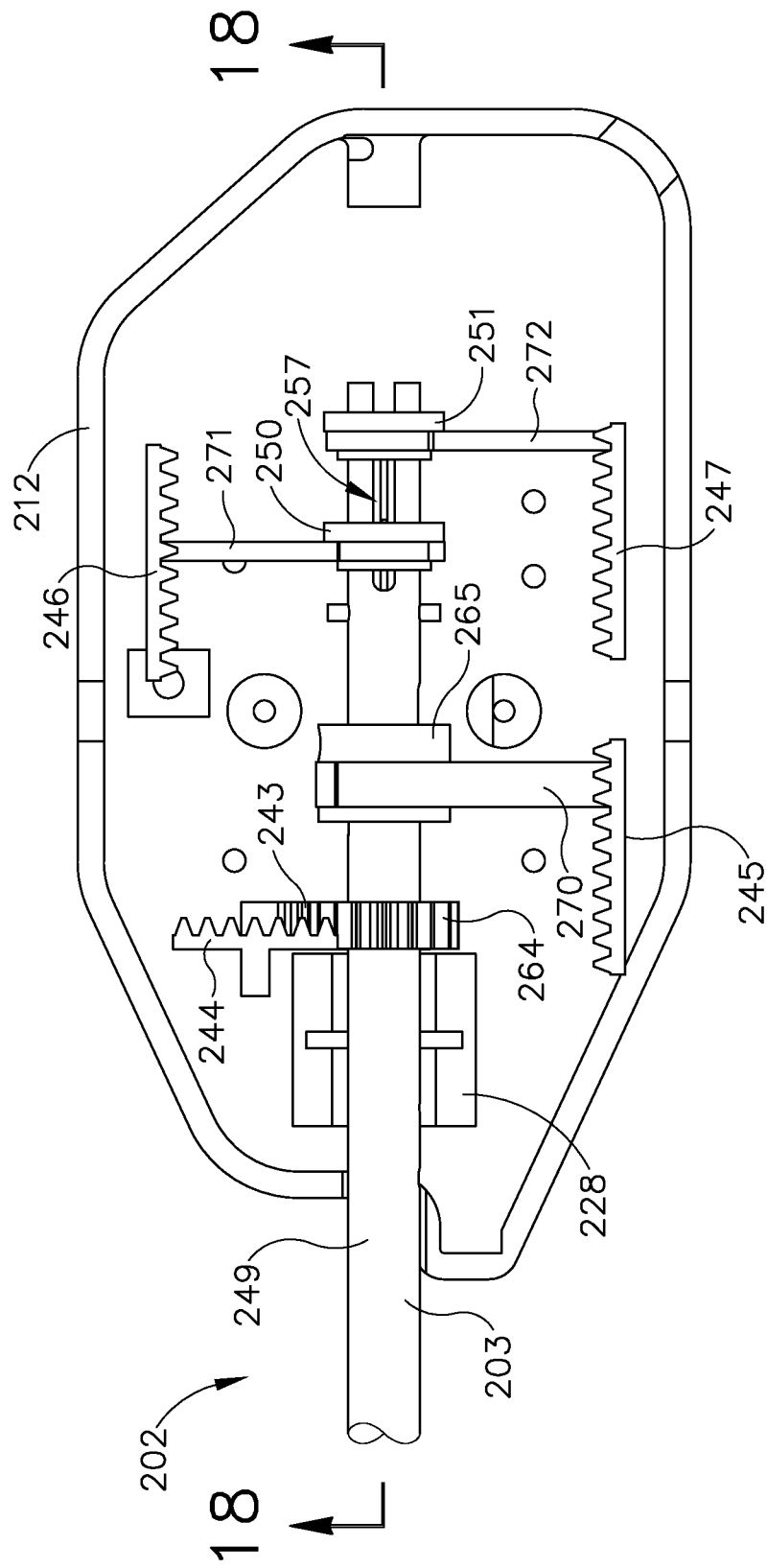
FIG. 17 depicts a bottom, plan view of the cover of the surgical instrument of FIG. 14.

FIG. 17 shows housing (212), which engages base (214). Shaft assembly (202) leads into housing (212). Housing (212) contains a half sleeve (228) shaped to engage a base cutout (229) (shown in FIG. 16) and is operable to receive a proximal portion (203) of shaft assembly (202).

Figure 18:
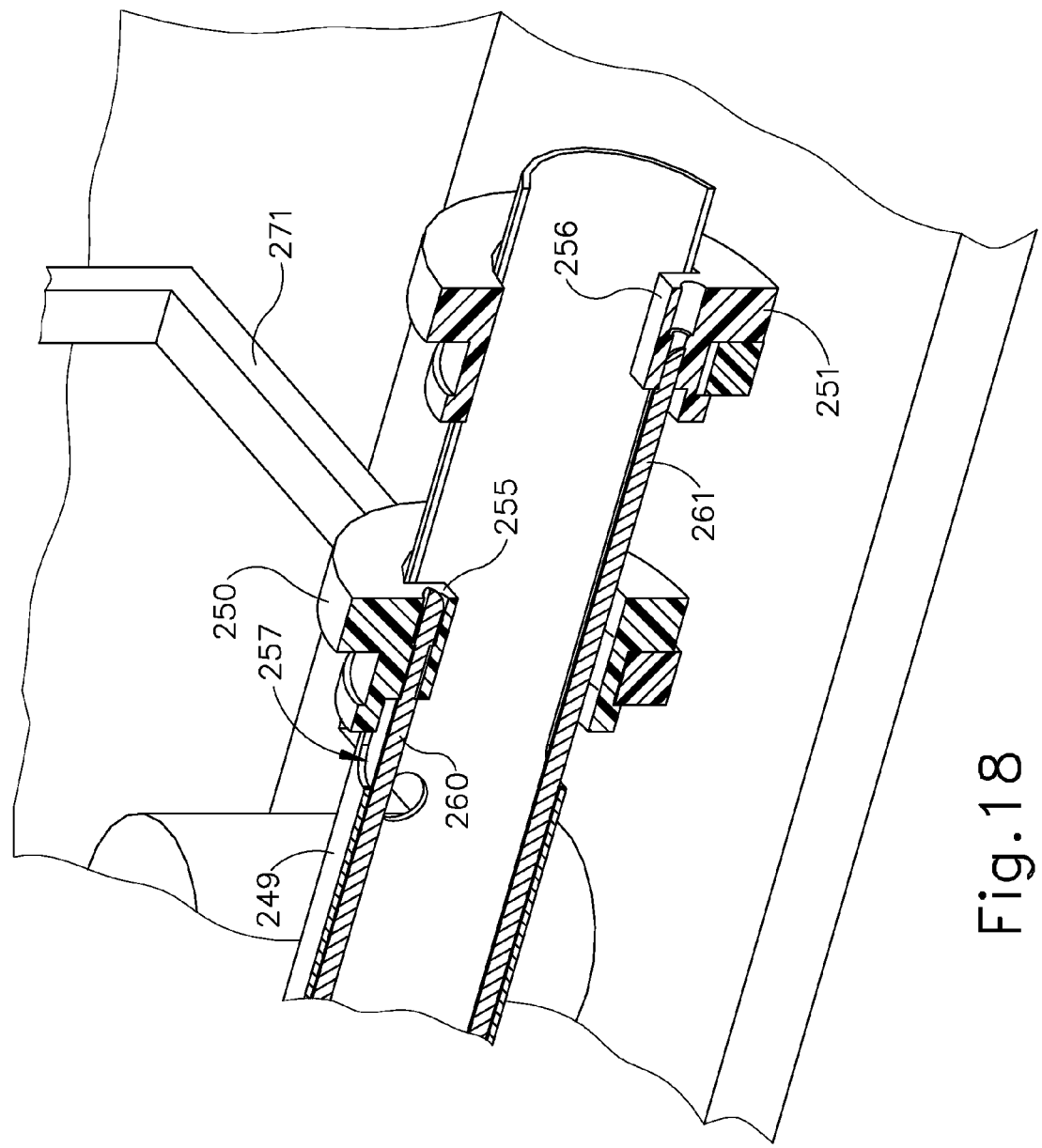
FIG. 18 depicts a side, perspective, cross sectional view of a shaft assembly of the surgical instrument of FIG. 14, taken along the line 18-18 of FIG. 17.
Figure 19:
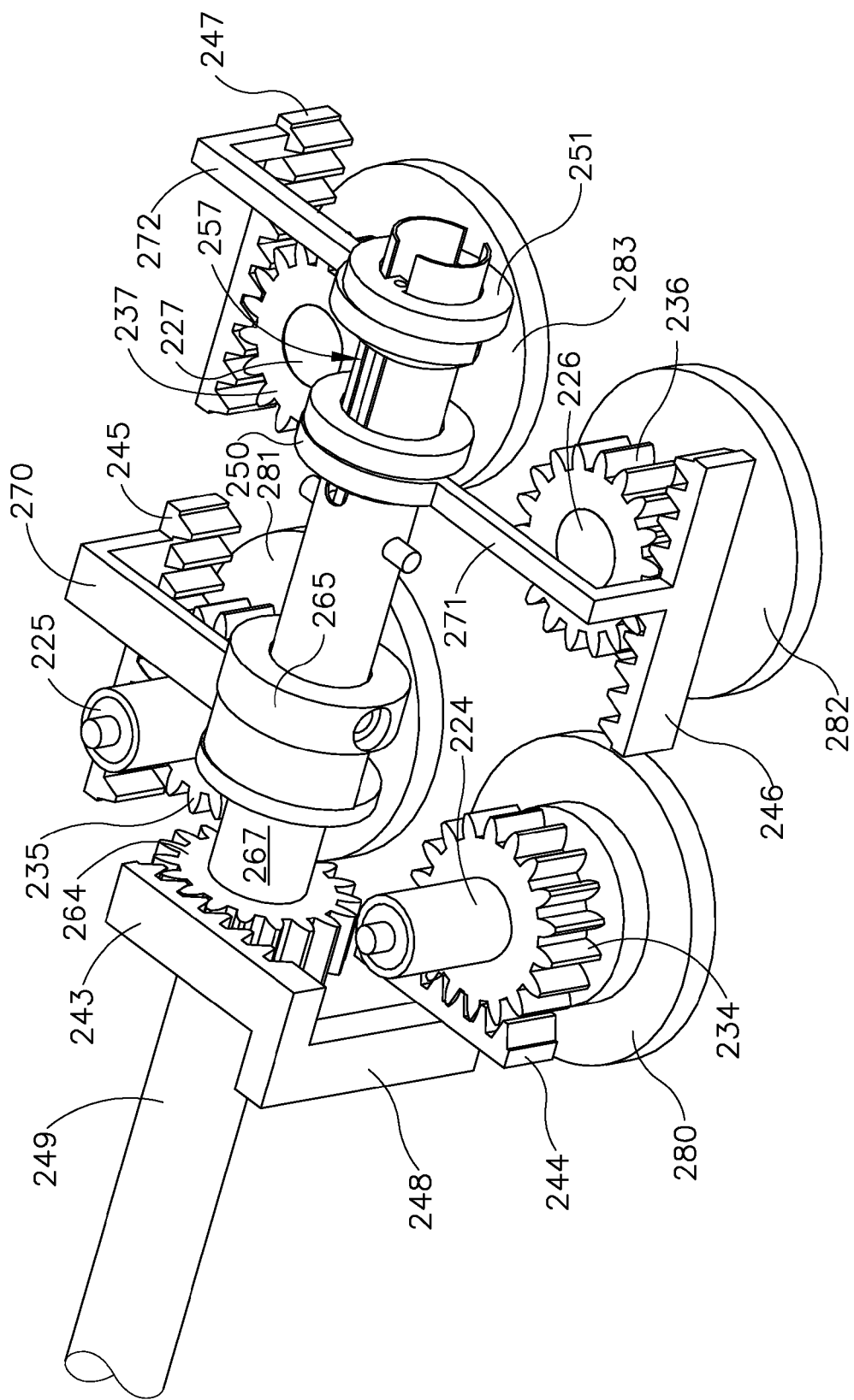
FIG. 19 depicts a rear, perspective, internal view of drive components of the surgical instrument of FIG. 14, showing racks engaging a plurality of spur gears.

FIGS. 17-19 show more of the components of shaft assembly (202). Shaft assembly (202) comprises a first rack (244), a first intermediate beam (248), a linking rack (243), a second rack (245), a second intermediate beam (270), a third rack (246), a third intermediate beam (271), a fourth rack (247), and a fourth intermediate beam (272). First rack (244) connects to linking rack (243) through first intermediate beam (248) such that when first rack (244) laterally translates, linking rack (243) laterally translates therewith in a unitary manner. Second rack (245) connects to firing ring (265) through second intermediate beam (270). Third rack (246) connects to first ring (250) through third intermediate beam (271). Fourth rack (247) connects to second ring (251) through fourth intermediate beam (272).

Turning to FIG. 18, shaft assembly (202) further comprises a tube (249) with a first articulation beam (260) and a second articulation beam (261) extending through tube (249). First articulation beam (260) and second articulation beam (261) are in communication with articulation region (204) and are operable to articulate end effector (206). When first articulation beam (260) pulls proximally, end effector (206) articulates toward first articulation beam (260); whereas when second articulation beam (261) pulls proximally, end effector (206) articulates toward second articulation beam (261). Shaft assembly (202) further comprises a first ring (250) and a second ring (251). First ring (250) is coupled with first articulation beam (260) and is also operable to move longitudinally along tube (249). As a result, when first ring (250) moves proximally or distally along the longitudinal axis of tube (249), first articulation beam (260) also moves proximally or distally within tube (249). Similarly, second ring (251) and second articulation beam (261) are coupled such that as second ring (251) move proximally or distally along longitudinal axis of tube (249), second articulation beam (261) translates proximally or distally with second ring (251). First ring (250) comprises a first ring block (255) that extends into tube (249) through a slot (257). Second ring (251) comprises a second ring block (256) that also extends into tube (249) through slot (257). First articulation beam (260) is anchored in first ring block (255), and second articulation beam (261) is anchored in second ring block (256). Slot (257) allows translation of first ring (250) and second ring (251) along slot (257). As a result, ring blocks (255, 256) are operable to pull articulation beams (260, 261) respectively. When articulation beam (260) is pulled proximally by the corresponding ring (250) to bend articulation section (204), articulation section (204) pulls distally on the other articulation beam (261). Second ring (251) is driven distally to accommodate this distal movement of articulation beam (261). Likewise, when articulation beam (261) is pulled proximally by the corresponding ring (251) to bend articulation section (204), articulation section (204) pulls distally on the other articulation beam (260); while first ring (250) is driven distally to accommodate this distal movement of articulation beam (260).

Turning to FIGS. 19 and 20, first spur gear (234) meshes with first rack (244), which is in communication with linking rack (243). First spur gear (234) meshes with first rack (244) upon closing housing (212) against base (214). Linking rack (243) meshes with shaft gear (264). As a result, when first spur gear (234) is rotated by first drive shaft (224), shaft gear (264) also rotates. In particular, when first spur gear (234) rotates CW (viewed from the top of instrument (200) down), shaft gear (264) rotates CW (viewed from the proximal end of instrument (200) distally) as well. Similarly, when first spur gear (234) rotates CCW, shaft gear (264) also rotates CCW. It will be appreciated that shaft gear (264) is rotationally coupled to end effector (206) such that rotating shaft gear (264) rotates end effector (206). In the exemplary version, shaft gear (264) is secured to tube (249) such that tube (249), articulation region (204), and end effector (206) all rotate together when shaft gear (264) rotated. Thus rotating first drive shaft (224) CW or CCW is operable to rotate end effector (206) in a similar manner.

Second spur gear (235) meshes with second rack (245) upon closing of housing (212) against base (214). Second rack (245) is in communication with a firing ring (265). Firing ring (265) may be coupled with a firing beam such as firing beam (190) shown in FIG. 9. For instance, firing ring (265) may be secured to a firing tube (267) slidably and coaxially disposed within tube (249). Firing beam (190) may be secured to the distal end of firing tube (267) such that advancing firing tube (267) advances firing beam (190). As a result, when second drive shaft (225) is rotated, second spur gear (235) also rotates, which moves second rack (245) and accordingly, firing ring (265), which in turn moves a firing beam longitudinally along shaft assembly (202). Thus, rotating second drive shaft (225) in one direction, such as CW (viewed from the top of instrument (200) down) in the illustrated version, longitudinally retracts the firing beam, whereas rotating second drive shaft (225) CCW (viewed from the top of instrument (200) down) longitudinally advances the firing beam.

Third spur gear (236) meshes with third rack (246) such that rotating third spur gear (236) causes third rack (246) to advance distally or retract proximally along an axis parallel to the longitudinal axis of tube (249). Similarly, fourth spur gear (237) meshes with fourth rack (247) such that rotating fourth spur gear (237) causes fourth rack (247) to advance distally or retract proximally along an axis parallel to the longitudinal axis of tube (249). It will be appreciated that third spur gear (236) engages third rack (246) and fourth spur gear (237) engages fourth rack (247) upon closing housing (212) upon base (214). Third rack (246) is in communication with first ring (250) and fourth rack (247) is in communication with second ring (251). As mentioned above, first ring (250) and second ring (251) are in communication with first articulation beam (260) and second articulation beam (261), respectively such that rotation of third spur gear (236) advances or retracts third rack (246), thereby causing first ring (250) to advance or retract to move first articulation beam (260) distally or proximally. Similarly, when fourth spur gear (237) rotates, the rotation causes fourth rack (247) to advance or retract, which also causes second ring (251) to advance or retract, thereby advancing or retracting second articulation beam (261).

First articulation beam (260) and second articulation beam (261) are positioned at opposite sides of tube (249). Furthermore, it will be appreciated that first ring (250) and second ring (251) may be configured to move longitudinally in opposing directions along tube (249). As a result, when first articulation beam (260) moves distally along tube (249), second articulation beam (261) moves proximally, and when first articulation beam (260) moves proximally, second articulation beam (261) moves distally. Thus, first articulation beam (260) and second articulation beam (261) are operable to provide an opposing pushing and pulling motion by their opposing advancing and retracting motion. It will be understood that pushing and pulling of first articulation beam (260) and second articulation beam (261) are operable to function similarly to articulation beams (174, 176) of FIG. 6, which are operable to articulate end effector (180) described above.

As mentioned above, racks (244, 245, 246, 247) and gears (234, 235, 236, 237) engage each other as a result of housing (212) closing against base (214). It will be understood that prior to snapping housing (212) to base (214), rotation of drive shafts (224, 225, 226, 227) does not engage racks (244, 245, 246, 247).

Thus, in one exemplary use, the end effector (180), such as one described above, may be rotated by rotating first drive shaft (224). Third drive shaft (226) and fourth drive shaft (227) may be rotated to articulate end effector (180). Finally, second drive shaft (225) may be rotated to cause a firing beam (190) such as one described above to advance distally along shaft assembly (202) such that jaws (182, 184) as described above are closed and tissue therebetween is cut and sealed. It will be appreciated that while the exemplary version contemplates an electrosurgical end effector (180), other suitable end effectors (180) may be used as would be apparent to one of ordinary skill in the art in view of the teachings herein.

Figure 21:
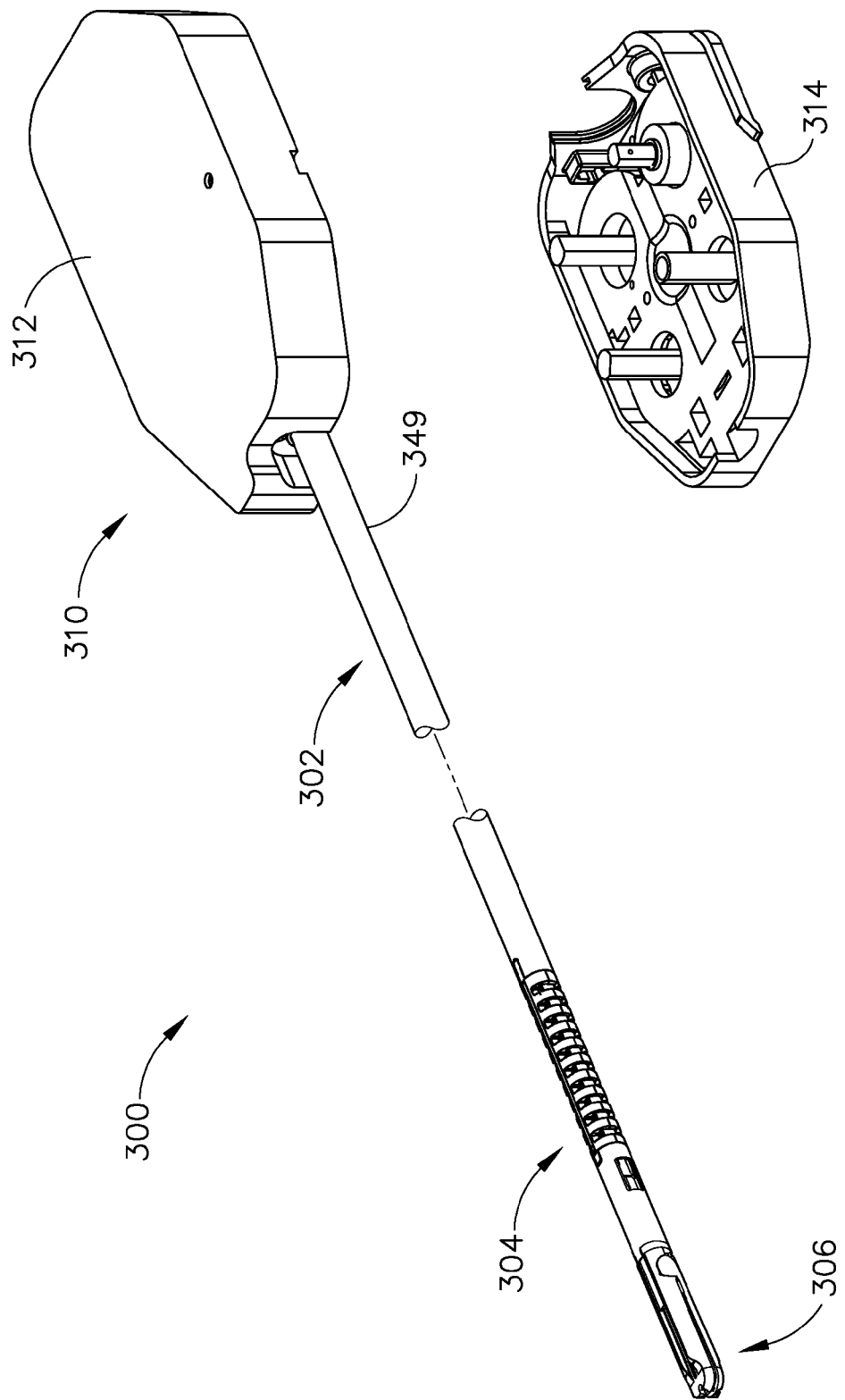
FIG. 21 depicts a top, perspective view of an exemplary alternative surgical instrument for incorporation with the system of FIG. 1, with D-shaped shafts.

IV. Exemplary Alternative Electrosurgical Instrument with Articulation Feature and Keyed Shafts FIG. 21 shows another exemplary alternative electrosurgical instrument (300). Instrument (300) of this example is substantially similar to instrument (100) described above in that instrument (300) has a shaft assembly (302), an articulation section (304), and an end effector (306) that are substantially identical to shaft assembly (160), articulation section (170), and end effector (180) described above. Instrument (300) of this example is also operable to couple with a dock (72) of robotic arm cart (40) via an interface assembly (310). However, interface assembly (310) of this example is different from interface assembly (110) described above.

Interface assembly (310) comprises a housing (312) and base (314). Shaft assembly (302) is an integral feature of housing (312) as seen in FIG. 21. Housing (312) is operable to snap onto base (314). Detailed engagement of housing (312) with base will be discussed in further detail below.

Figure 22:
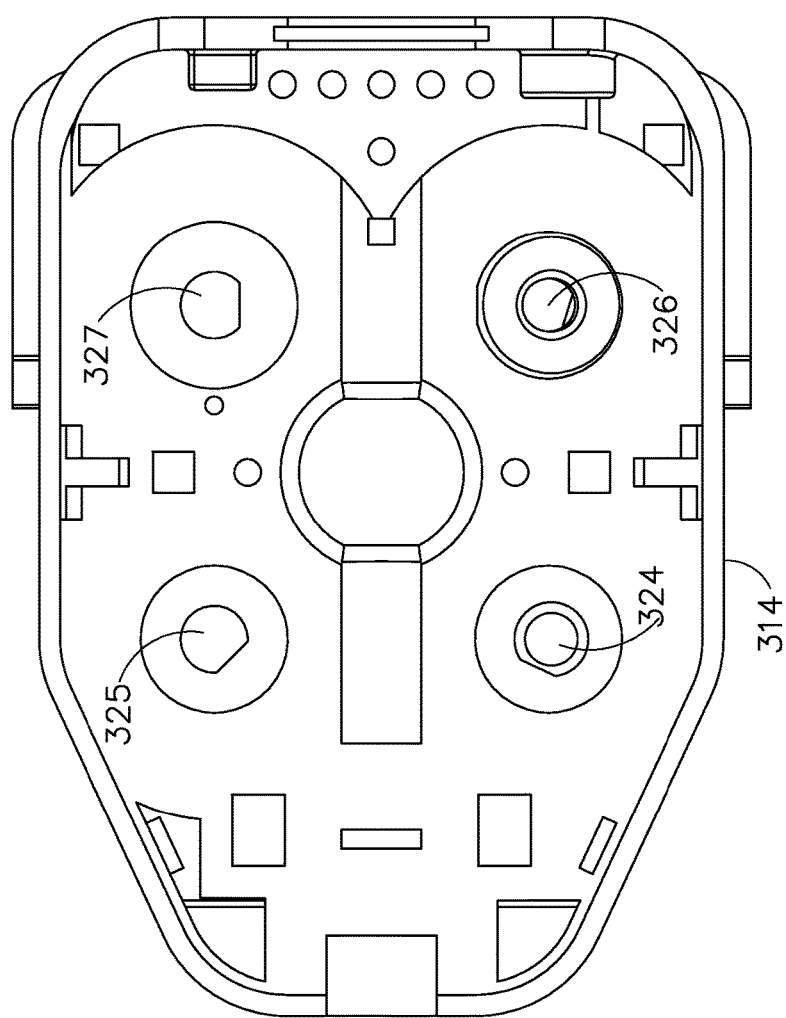
FIG. 22 depicts a top, plan view of the base of the surgical instrument of FIG. 21 showing the D-shaped shafts.
Figure 25:
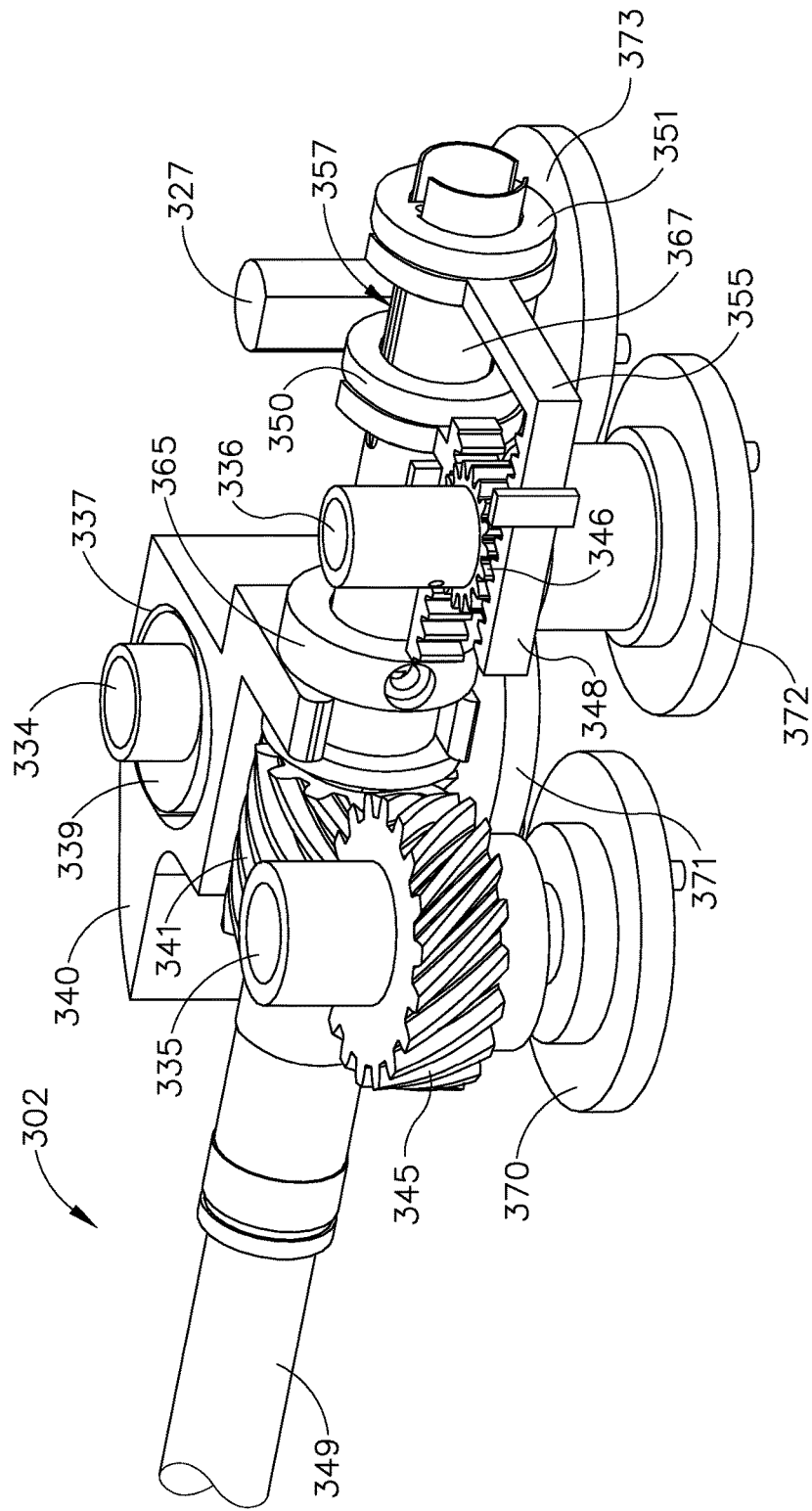
FIG. 25 depicts a perspective, internal view of drive components of the surgical instrument of FIG. 21 showing the D-shaped shafts engaging the D-shaped holes.

As seen in FIG. 22, base (314) comprises a first drive shaft (324), a second drive shaft (325), a third drive shaft (326), and a fourth drive shaft (327). It will be appreciated that base (314) is operable to engage dock (72) such that dock (72) can cause drive shafts (324, 325, 326, 327) to rotate. As shown in FIG. 25, drive shafts (324, 325, 326, 327) are secured to respective drive discs (370, 371, 372, 373), which are substantially similar to drive discs (120) shown in FIG. 10 and described above. Drive discs (370, 371, 372, 373) may thus be controlled through instrument dock (72) by a user to rotate drive shafts (324, 325, 326, 327). Each drive shaft (324, 325, 326, 327) has a contoured, non-circular shape configured for receipt in a drive shaft opening, as will be discussed in further detail below. In the illustrated version, each drive shaft (324, 325, 326, 327) has a D-shape cross section, though it will be appreciated that other suitable shapes for drive shafts (324, 325, 326, 327) may be used as would be apparent to one of ordinary skill in the art in view of the teachings herein.

Figure 23:
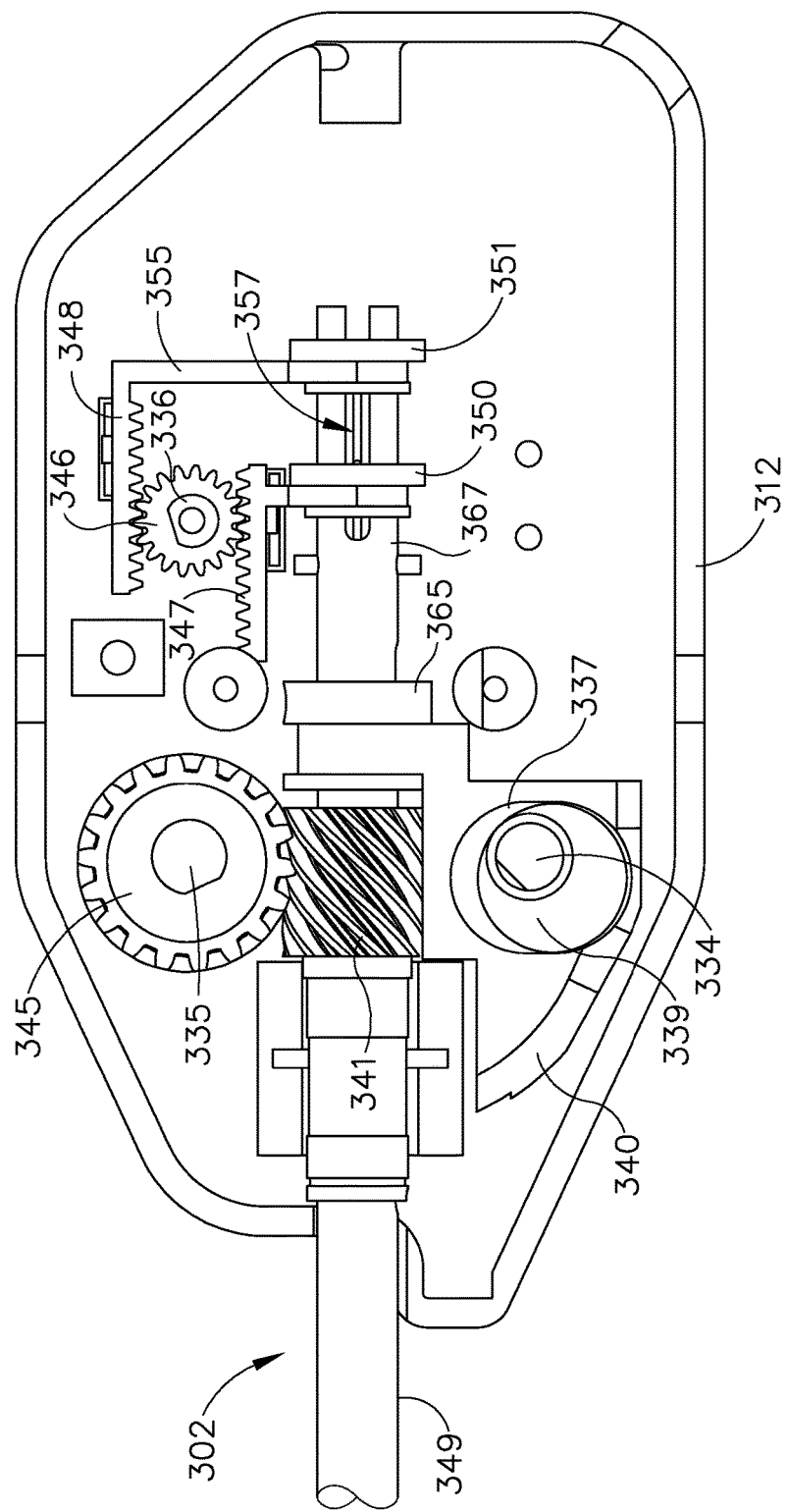
FIG. 23 depicts a bottom, plan view of the housing of the surgical instrument of FIG. 21 showing D-shaped holes.
Figure 24:
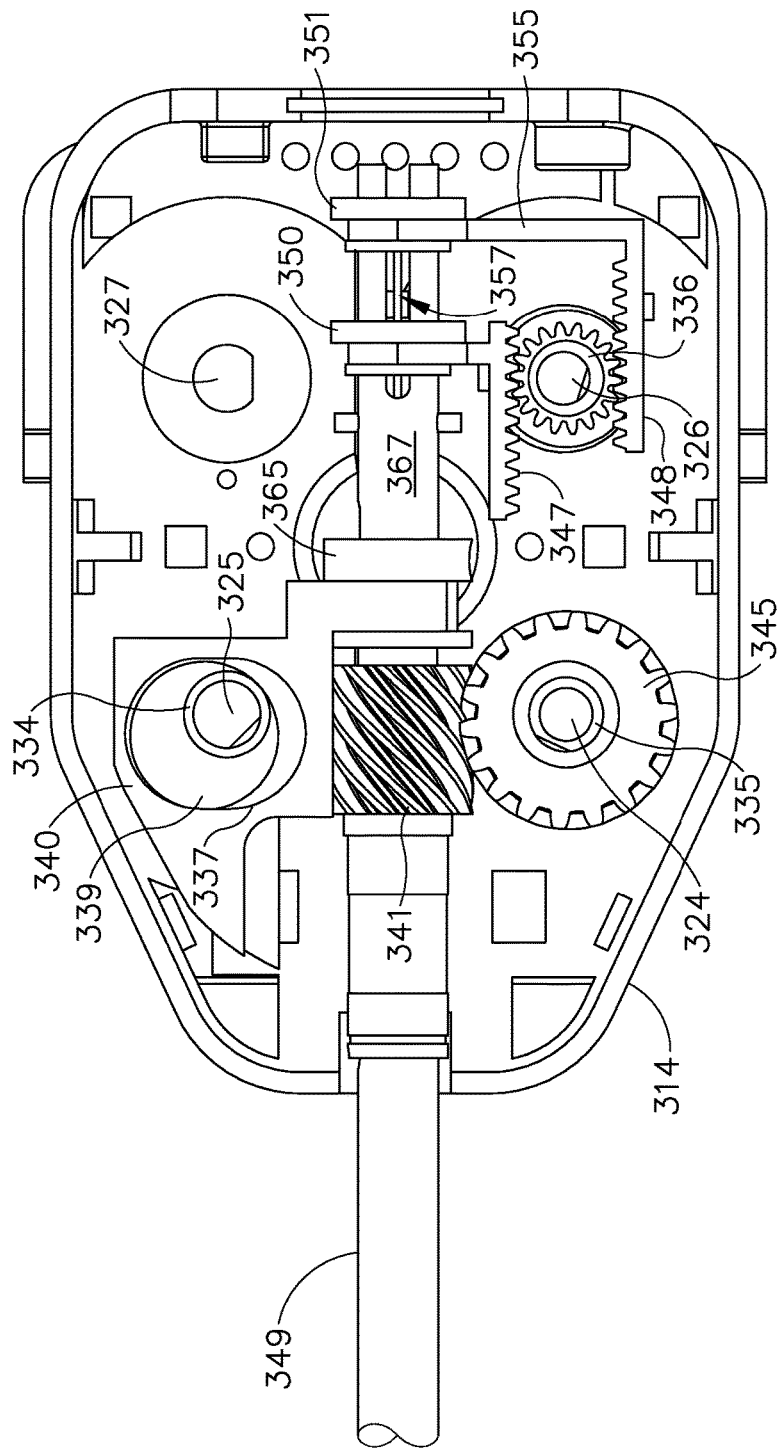
FIG. 24 depicts a top, plan view of the base of the surgical instrument of FIG. 21, with a shaft assembly and drive components of the housing engaged with the D-shaped shafts of the base, but with the housing shell omitted for clarity.

Shaft assembly (302) is partially contained within housing (312). As seen in FIG. 23, housing (312) contains a circular cam (339) defining a first drive shaft opening (334). Housing (312) further contains a drive helical gear (345) defining a second drive shaft opening (335). Finally, housing (312) contains a second spur gear (346) that defines a third drive shaft opening (336). Drive shaft openings (334, 335, 336) complement the shape of drive shafts (324, 325, 326). As a result, drive shafts (324, 325, 326) rotate, circular cam (339), drive helical gear (345), and second spur gear (346) also rotate. It will be appreciated that even though the exemplary version uses a D-shaped drive shafts (324, 325, 326) and corresponding openings (334, 335, 336), other suitable shapes operable to complement shafts (324, 325, 326) with openings (334, 335, 336) may be used as would be apparent to one of ordinary skill in the art in view of the teachings herein. For instance, hex, star, elliptical, half circles, etc. may be used instead of the D-shape. Second drive shaft opening (335) as mentioned above is defined by an offset opening made in circular cam (339), which fits within an elongated opening (337) of a drive block (340). As seen in FIG. 24, circular cam (339) is positioned within elongated opening (337) such that as circular cam (339) rotates, drive block (340) advances or retracts longitudinally along the longitudinal axis of shaft assembly (302). Furthermore, drive block (340) engages a firing ring (365) that may be secured to a firing tube (367) slidably and coaxially disposed within tube (349). A firing beam, such as one described above may be secured to the distal end of firing tube (367). Therefore, rotating first drive shaft opening (334) is operable to advance or retract a firing beam within shaft assembly (302).

Second drive shaft opening (335) is formed through the center of a drive helical gear (345). Drive shaft (324) is disposed in second drive shaft opening (335) such that drive helical gear (345) rotates with drive shaft (324). Drive helical gear (345) meshes with a shaft helical gear (341) that is secured to shaft assembly (302). As a result, rotation of drive shaft (324) and drive helical gear (345) causes shaft assembly (302) to rotate.

Shaft assembly (302) further comprises a second spur gear (346) through which third drive shaft opening (336) extends. Second spur gear (346) meshes with a first rack (347) and a second rack (348). It will be appreciated that as second spur gear (346) rotates, racks (347, 348) move in opposing directions. As seen in FIG. 24, if second spur gear (346) rotates CCW (viewed from the top down), then first rack (347) advances longitudinally toward the distal end of shaft assembly (302), while second rack (348) retracts longitudinally away from the distal end of shaft assembly (302). Accordingly, when second spur gear (346) rotates CW (viewed from the top down), first rack (347) retracts away from the distal end of shaft assembly (302) and second rack (348) advances longitudinally toward the distal end of shaft assembly (302). First rack (347) is in communication with first ring (350) and second rack (348) is in communication with a second ring (351). Second rack (348) connects to second ring (351) via a linking beam (355). Rings (350, 351) are operable to move toward each other longitudinally along tube (349) or away from each other. It will be appreciated that rings (350, 351) are in communication with beams substantially similar to articulation beams (260, 261) described above. Rings (350, 351) are able to engage beams through slot (357), which accommodates rings (350, 351) to slidingly translate along tube (349). Beams within tube (349) are operable to articulate end effector (306). Thus moving rings (350, 351) toward and away from each other are operable to move beams within shaft assembly (302), which are then operable to articulate end effector (306).

FIGS. 24-25 show shaft assembly (302) engaging drive shafts (324, 325, 326, 327), when housing (312) is connected to base (314). For visibility purposes, housing has been omitted from FIG. 24; and housing (312) and base (314) have both been omitted in FIG. 25. As shown, first drive shaft (324) engages second drive shaft opening (335) and second drive shaft (325) engages first drive shaft opening (334). Third drive shaft (326) engages third drive shaft opening (336). Fourth drive shaft (327) does not engage anything in the exemplary version, though it will be understood that fourth drive shaft (327) may engage any suitable component operable to utilize the rotation and keyed shape aspects of fourth drive shaft (327).

Figure 26:
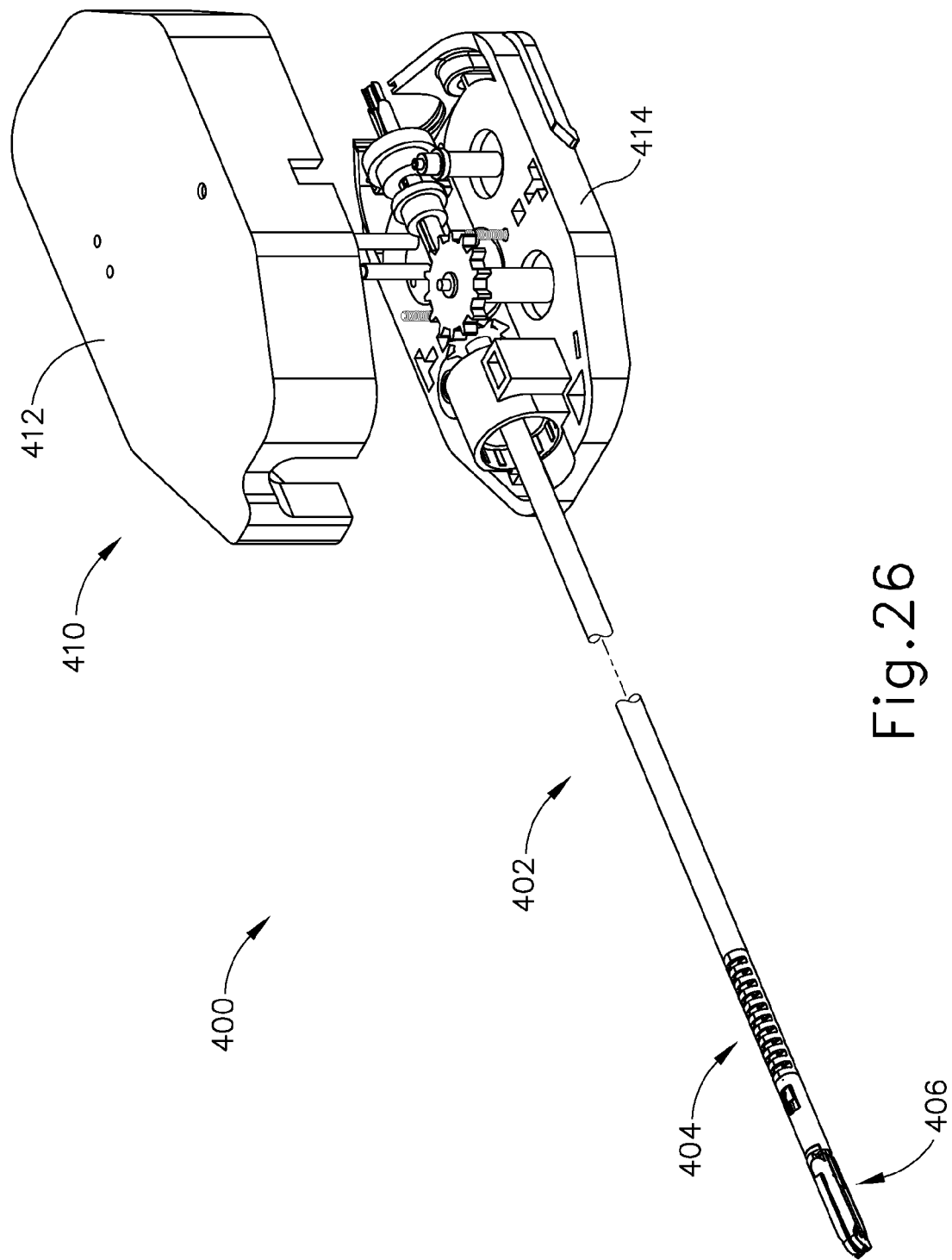
FIG. 26 depicts a top, perspective view of an exemplary alternative surgical instrument for incorporation with the system of FIG. 1.

V. Exemplary Alternative Electrosurgical Instrument with Articulation Feature and Bevel Gear FIG. 26 shows another exemplary alternative electrosurgical instrument (400). Instrument (400) of this example is substantially similar to instrument (100) described above in that instrument (400) has a shaft assembly (402), an articulation section (404), and an end effector (406) that are substantially identical to shaft assembly (160), articulation section (170), and end effector (180) described above. Instrument (400) of this example is also operable to couple with a dock (72) of robotic arm cart (40) via an interface assembly (410). Interface assembly (410) of this example may be substantially similar to any of the previously described interface assemblies (210, 310). However, interface assembly (410) differs in the mechanism used to rotate shaft assembly (402).

Figure 27:
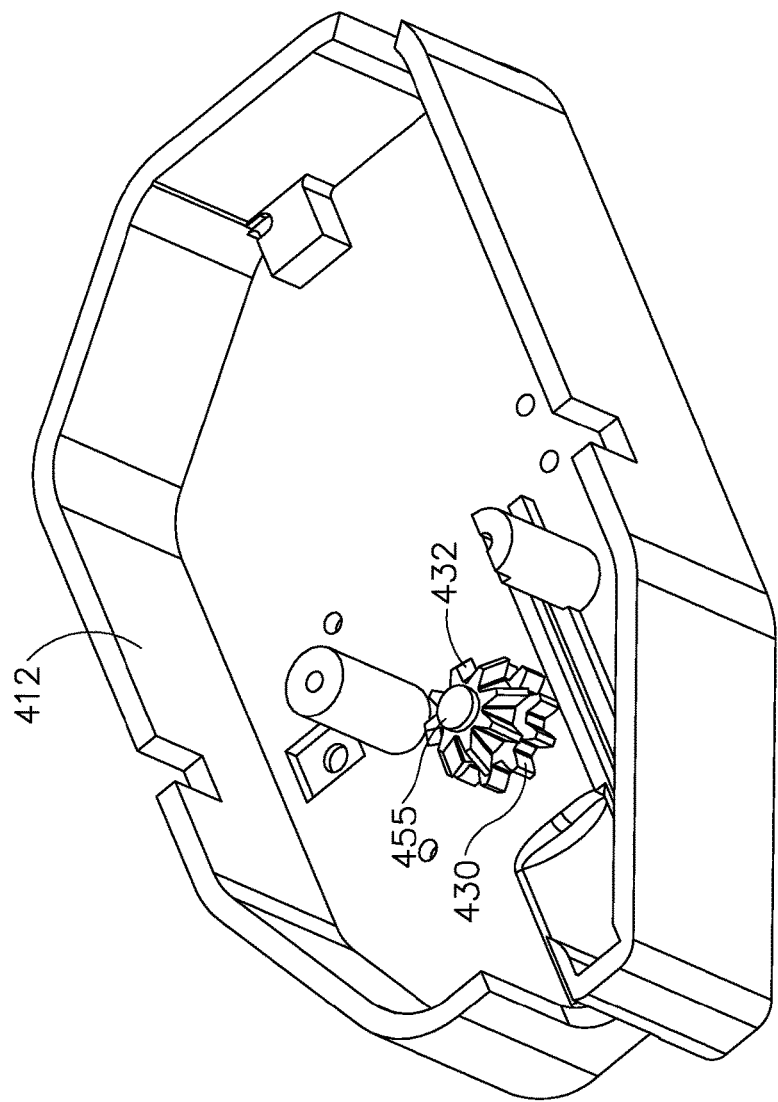
FIG. 27 depicts a bottom, perspective view of the cover of the surgical instrument of FIG. 26 showing a bevel gear.

Interface assembly (410) comprises a housing (412) and base (414). Turning to FIG. 27, housing (412) has a first spur gear (430) and a bevel gear (432). It will be understood that housing (412) could hold other components including any of the previously described components. First spur gear (430) and bevel gear (432) are rotationally coupled such that when first spur gear (430) rotates, bevel gear (432) also rotates. In particular, first spur gear (430) and bevel gear (432) are coaxially aligned and secured to a common shaft (455), which rotates freely relative to housing (412).

Figure 28:
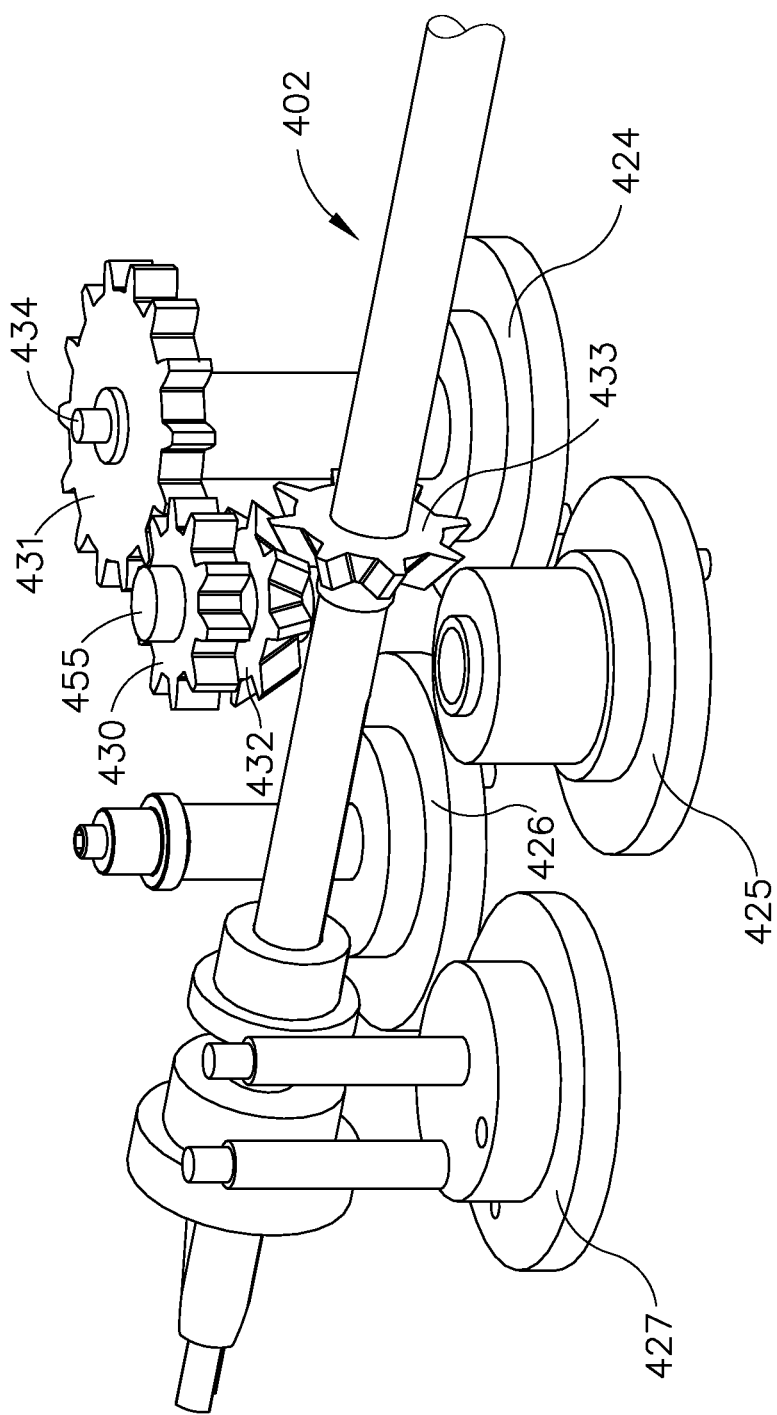
FIG. 28 depicts a side, perspective, internal view of the surgical instrument of FIG. 26 with the bevel gear engaging the shaft assembly.

FIG. 28 shows housing (412) attached to base (414) such that the internal components engage. However, for visibility of components contained in housing (412), housing (412) and base (414) have been omitted from the illustration. Base (414) includes a first drive shaft and disc combination (424), a second disc (425), a third disc (426), and a fourth disc (427). First drive shaft and disc combination (424) and discs (425, 426, 427) are substantially similar to drive discs (120) shown in FIG. 10 and described above. Bevel gear (432) is in rotational communication with shaft assembly (402) through a shaft bevel gear (433) such that when bevel gear (432) rotates, shaft assembly (402) also rotates accordingly. For instance, when bevel gear (432) rotates CW (looking from the top of instrument (400) toward the bottom of instrument (400)), shaft bevel gear (433) rotates CW (looking from the proximal end of instrument (400) toward the distal end of instrument (400)) thereby rotating shaft assembly (402) CW. Similarly, when bevel gear (432) rotates CCW, shaft assembly (402) also rotates CCW.

First spur gear (430) meshes with a second spur gear (431). Furthermore, second spur gear (431) is secured to a first drive shaft (434) such that when first drive shaft (434) rotates, second spur gear (431) rotates, thereby causing first spur gear (431) to rotate. Once first spur gear (431) rotates, bevel gear (432) rotates to communicate rotation to shaft bevel gear (433), causing shaft assembly (402) to rotate too. It will be understood that the configuration shown in FIGS. 26-28 may be interchangeably used to rotate any of shaft assemblies (302, 202) as shown above. Similarly, any of the articulation and firing beam actuation features described herein could be readily incorporated into base (414). Other suitable configurations and uses for interface assembly (410) will be apparent to one of ordinary skill in the art in view of the teachings herein.

Figure 29:
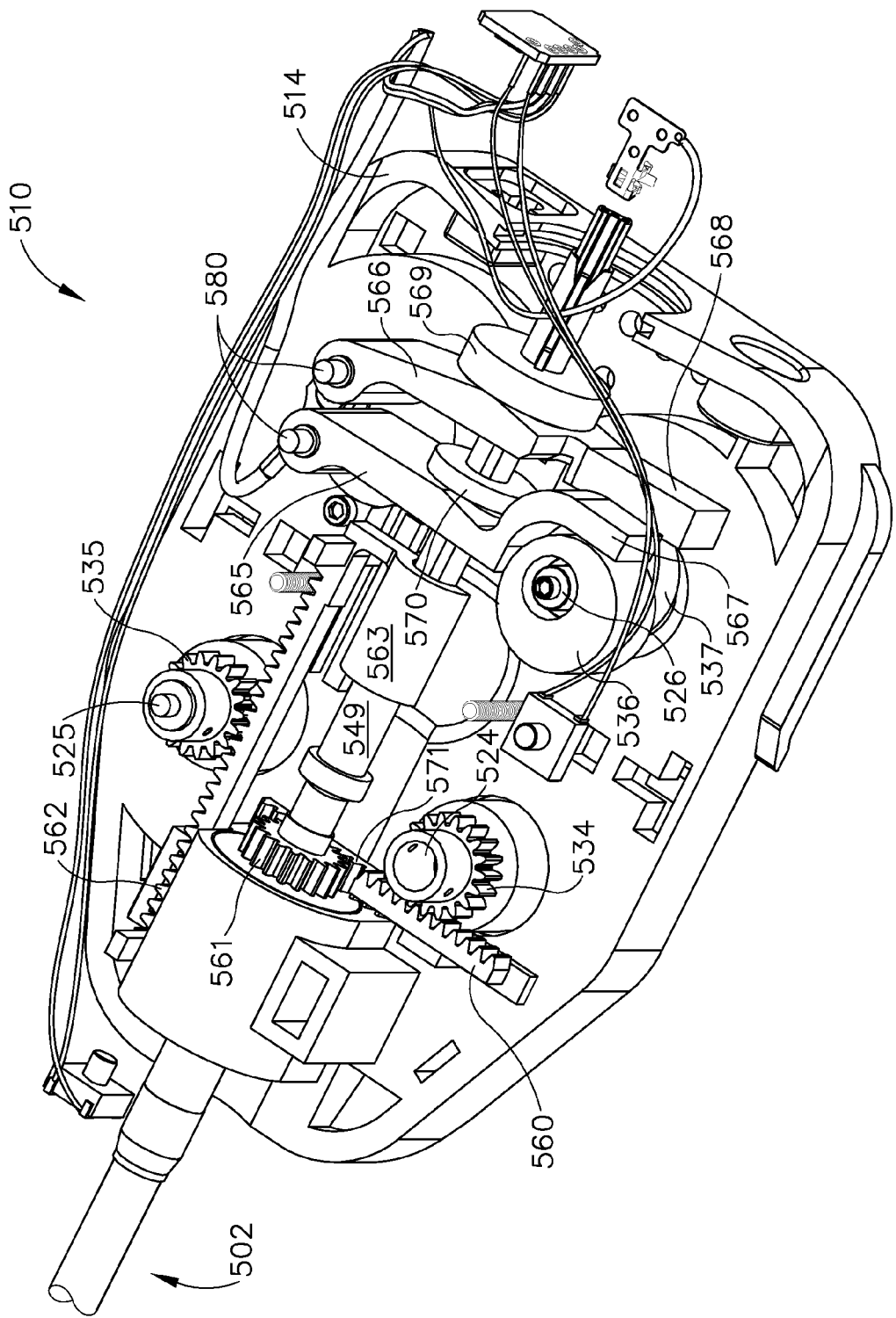
FIG. 29 depicts a top, perspective view of an alternative interface assembly for use with the surgical instrument of FIG. 1.

VI. Exemplary Alternative Electrosurgical Instrument with Articulation Feature and Dual Rack and Pinion FIG. 29 shows an exemplary alternative interface assembly (510) operable for use with various surgical instruments such as instrument (100), etc. Interface assembly (510) comprises a base (514), a first drive shaft (524), a second drive shaft (525), and a third drive shaft (526).

Figure 30:
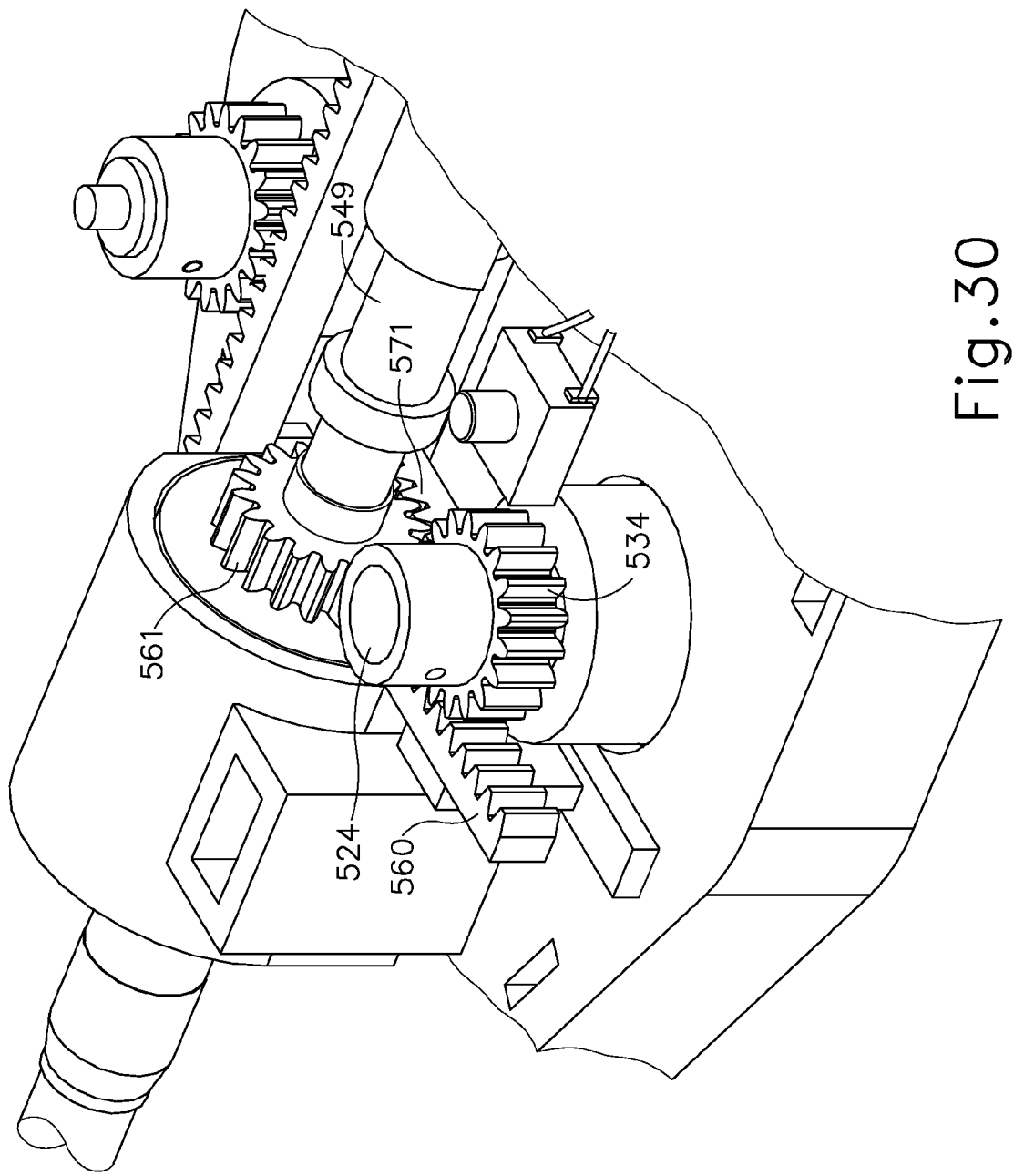
FIG. 30 depicts an enlarged perspective view of the interface assembly of FIG. 29 showing the first drive shaft, first rack, and second rack.

First drive shaft (524) is operable to rotate tube (549) of shaft assembly (502). First drive shaft (524) is unitarily coupled with a first spur gear (534), which meshes with a first rack (560). First rack (560) is in communication with a second rack (571), and second rack (571) is in communication with a shaft gear (561). Connection between first rack (560) and second rack (571) may be seen more clearly in FIG. 30. As seen in the illustrated version, first rack (560) and second rack (571) are parallel to one another, but facing in perpendicular directions. First rack (560) faces first spur gear (534) and second rack (571) faces upward at shaft gear (561). Shaft gear (561) is unitarily coupled with tube (549) such that rotation of shaft gear (561) rotates tube (549) and as a result rotates shaft assembly (502). This rotation is operable to rotate shaft assembly (502). Thus, a result, rotation of first drive shaft (524) is operable to cause rotation of shaft assembly (502).

Returning to FIG. 29, second drive shaft (525) is in unitary communication with a second spur gear (535). Second spur gear (535) meshes with a third rack (562) such that rotation of second drive shaft (525) is operable to move third rack (562) longitudinally parallel to tube (549) Third rack (562) is in communication with a firing sleeve (563). Firing sleeve (563) is in communication with a firing beam as described above. It will be appreciated that firing sleeve (563) may be in communication with any suitable component operable to move longitudinally along tube (549). As a result, rotating second drive shaft (525) is operable to drive firing sleeve (563) and accordingly a firing beam.

Third drive shaft (526) is in communication with an upper cam (536) and a lower cam (537). Third drive shaft (526) extends through upper cam (536) and lower cam (537) in an offset manner such that third drive shaft (526) does not extend coaxially through upper and lower cylinders (536, 537) and such that cylinders (536, 537) are eccentrically positioned on drive shaft (526) in an opposing manner. A first camming arm (565) includes a rounded arm portion (567), which contacts upper cam (536). Lower cam (537) contacts a straight arm portion (568) of a second camming arm (566). First and second camming arms (565, 566) are pivotally held by pins (580). Arm portions (567, 568) are vertically offset from each other, enabling portions (567, 568) to pass through a common vertical plane when arms (565, 566) are pivoted in an opposing fashion.

First and second camming arms (565, 566) are in communication with beams such as articulation beams (260, 261) of FIG. 17. In particular, first camming arm (565) longitudinally engages first ring (570), which is coupled with a first articulation beam (not shown) that is similar to beam (260). Second camming arm (566) engages second ring (261), which is coupled with a second articulation beam (not shown) that is similar to beam (261). These articulation beams are operable to provide articulation of an end effector as described above.

Upper and lower cylinders (536, 537) are rotated simultaneously such that only one cylinder (536, 537) drives the corresponding camming arm (565, 566) proximally one at a time. In particular, upper cylinder (536) either drives first camming arm (565) and rounded arm (567) proximally or allows first camming arm (565) and rounded arm (567) to pivot distally. In an opposing manner, lower cylinder (537) either drives second camming arm (566) and straight arm (568) proximally or allows second camming arm (566) and straight arm (568) to pivot distally. It will be understood that the proximal pivoting of first camming arm (565) and rounded arm (567) will cause second camming arm (566) and straight arm (568) to pivot distally due to first camming arm (565) pulling on an end effector at an articulation section, which then pulls second camming arm (566) distally, which maintains a pulling bias between straight arm (568) and lower cam (537). In an opposing manner, proximal pivoting of second camming arm (566) and straight arm (568) pulls on an end effector at an articulation section, which pulls on first camming arm (565) and rounded arm (567), which maintains a distal bias between rounded portion (567) and upper cam (536). It will be appreciated that first and second camming arms (565, 566) are positioned such that rotation of upper and lower cylinders (536, 537) causes first and second camming arms (565, 566) to sequentially pivot toward each other and pivot away from each other. As a result, the motion of camming arms (565, 566) is operable to drive articulation in shaft assembly (502). Thus, rotation of third drive shaft (526) is operable to cause articulation of a distal portion of shaft assembly (502).

Figure 31:
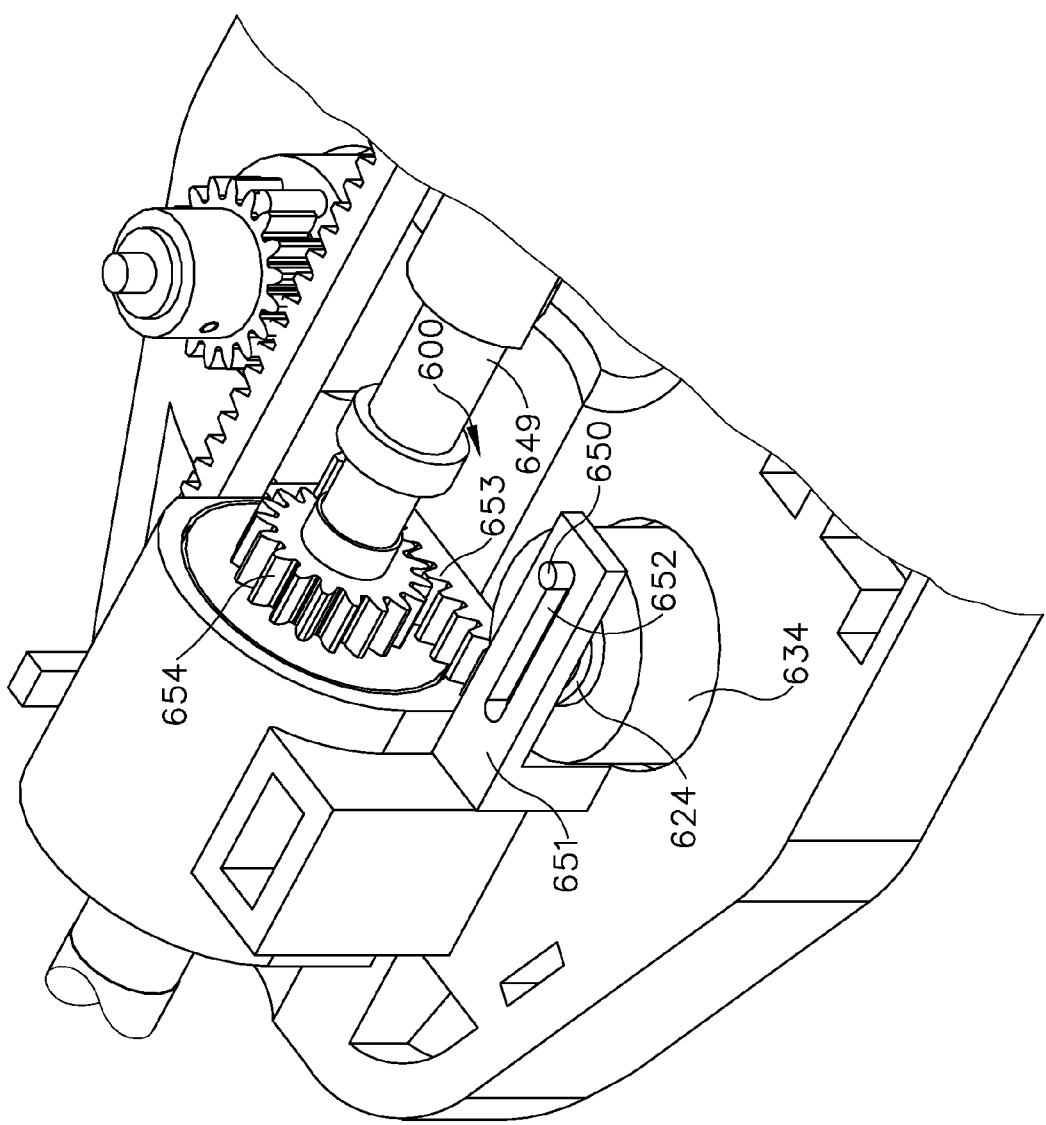
FIG. 31 depicts a top, perspective view of a first drive assembly for use with the interface assembly of FIG. 29.

FIG. 31 shows an exemplary first drive assembly (600). It will be appreciated that first drive assembly (600) is operable to be interchangeable with first drive shaft (524), first spur gear (534), and first rack (560) of interface assembly (510) of FIG. 30. It will be understood that first drive assembly (600) may be used with any suitable interface assembly as would be apparent to one of ordinary skill in the art in view of the teachings herein. First drive assembly (600) is operable generally to rotate a shaft gear (654) in communication with a tube (649), which is operable ultimately to rotate a shaft assembly such as shaft assembly (502) as described above.

First drive assembly (600) comprises a first drive shaft (624). First drive shaft (624) includes a peg (650) eccentrically located at the perimeter of first drive shaft (624). Peg (650) fits within a slot (652) formed in a linking member (651). As a result, as first drive shaft (624) rotates, peg (650) urges linking member (651) laterally back and forth. Linking member (651) is in communication with first rack (653), which meshes with shaft gear (654). Thus, first drive shaft (624) is operable to rotate to cause tube (649) to rotate.

VII. Miscellaneous

It should be understood that an interface assembly may include an integral power source such as a battery, and that such a battery may provide at least some of any electrical power required to operate the surgical instrument of the interface assembly. In other words, an interface assembly may provide electrical power to one or more components of the associated surgical instrument from a source that is internal to the interface assembly and/or from a source that is external to the interface assembly (e.g., through system (10)). Regardless of where the source is located, the interface assembly may include one or more conductive clips, contacts, and/or other features that provide automatic electrical coupling with the shaft assembly when the shaft assembly is mechanically coupled with the interface assembly. Various suitable ways in which a shaft assembly and an interface assembly may be electrically coupled will be apparent to those of ordinary skill in the art in view of the teachings herein.

Furthermore, an interface assembly may be configured to couple with a variety of types of modular shaft assemblies. Such modular shaft assemblies may provide inter-modality and/or intra-modality variation. Examples of inter-modality variation may include a single interface assembly being able to selectively couple with different shaft assemblies having a variety of end effectors that include staplers, RF electrosurgical features, ultrasonic cutting features, etc. Examples of intra-modality variation may include a single interface assembly being able to selectively couple with different RF electrosurgical shaft assemblies having a variety of end effectors that include straight jaws, curved jaws, etc. Other inter-modality variations and intra-modality variations will be apparent to those of ordinary skill in the art in view of the teachings herein.

It should also be understood that any of the versions of instruments described herein may include various other features in addition to or in lieu of those described above. By way of example only, any of the instruments described herein may also include one or more of the various features disclosed in any of the various references that are incorporated by reference herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc.

In versions where the teachings herein are applied to a surgical stapling instrument, it should be understood that the teachings herein may be combined with the teachings of one or more of the following, the disclosures of all of which are incorporated by reference herein: U.S. Pat. No. 7,380,696; U.S. Pat. No. 7,404,508; U.S. Pat. No. 7,455,208; U.S. Pat. No. 7,506,790; U.S. Pat. No. 7,549,564; U.S. Pat. No. 7,559,450; U.S. Pat. No. 7,654,431; U.S. Pat. No. 7,780,054; U.S. Pat. No. 7,784,662; and/or U.S. Pat. No. 7,798,386. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, now U.S. Pat. No. 8,461,744, issued on Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued on Jan. 27, 2015, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
(a) a surgical end effector;
(b) a shaft assembly, wherein the surgical end effector is coupled with the shaft assembly, wherein the shaft assembly defines a longitudinal axis, wherein the shaft assembly comprises a translating member extending through the shaft assembly, wherein the translating member is movable parallel to the longitudinal axis; and (c) an interface assembly structured and positioned to engage the shaft assembly, wherein the interface assembly comprises:
   (i) a plurality of independently rotatable drive shafts, wherein the plurality of drive shafts are parallel with each other, wherein the plurality of drive shafts are perpendicular to the shaft assembly, wherein the plurality of drive shafts includes a first drive shaft, wherein the drive shaft is rotatable about a first drive shaft axis, wherein the first drive shaft axis is perpendicular to the longitudinal axis of the shaft assembly, and
   (ii) a first rack in communication with the first drive shaft, wherein the first rack is further in communication with the shaft assembly, wherein the first drive shaft is structured and positioned to drive the first rack along a path that is parallel to the longitudinal axis of the shaft assembly.

2. The apparatus of claim 1, wherein the translating member of the shaft assembly comprises a firing beam, wherein the first rack is configured to drive the firing beam through the shaft assembly.

3. The apparatus of claim 1, wherein the shaft assembly includes an articulation section, wherein the first rack is structured and positioned to deflect the surgical end effector from the longitudinal axis at the articulation section.

4. The apparatus of claim 3, wherein the interface assembly further comprises a second rack in communication with the first drive shaft, wherein the second rack is further in communication with the shaft assembly, wherein the first drive shaft is structured and positioned to drive the second rack along a path that is parallel to the longitudinal axis of the shaft assembly.

5. The apparatus of claim 4, wherein the second rack is structured and positioned to deflect the surgical end effector from the longitudinal axis at the articulation section.

6. The apparatus of claim 5, wherein the first drive shaft is structured and positioned to drive the first and second racks simultaneously in opposing directions along respective paths that are parallel to the longitudinal axis of the shaft assembly.

7. The apparatus of claim 1, wherein the interface assembly comprises a base portion and a housing portion, wherein the first drive shaft is integral with the base portion, wherein the first rack is integral with the housing portion.

8. The apparatus of claim 7, wherein the shaft assembly is integral with the housing portion.

9. The apparatus of claim 7, wherein the interface assembly further comprises a pinion coupling the first drive shaft with the first rack, wherein the pinion is integral with the housing portion.

10. The apparatus of claim 9, wherein the first drive shaft has a non-circular cross-section, wherein the pinion defines a non-circular opening having a shape complementing the cross-section of the first drive shaft.

11. The apparatus of claim 1, wherein the shaft assembly is configured to selectively engage a portion of the interface assembly along a path that is transverse to the longitudinal axis of the shaft assembly.

12. The apparatus of claim 1, wherein the first drive shaft is secured to a drive disc having a pair of coupling pins, wherein the coupling pins are configured to couple with a dock of a robotic drive system.

13. The apparatus of claim 1, wherein the plurality of drive shafts further includes a second drive shaft, wherein the second drive shaft is rotatable about a second drive shaft axis, wherein the second drive shaft axis is perpendicular to the longitudinal axis of the shaft assembly, wherein the interface assembly further comprises a second rack in communication with the second drive shaft, wherein the second drive shaft is structured and positioned to drive the second rack along a path that is perpendicular to the longitudinal axis of the shaft assembly.

14. The apparatus of claim 13, wherein the shaft assembly includes an outer gear fixed to the shaft assembly, wherein the second rack meshes with the outer gear such that the second rack is structured and positioned to rotate the shaft assembly via the outer gear.

15. The apparatus of claim 1, wherein the plurality of drive shafts further includes a second drive shaft, wherein the second drive shaft is structured and positioned to translate the translating member within the shaft assembly.

16. The apparatus of claim 15, further comprising a cam cylinder eccentrically disposed on the second drive shaft, wherein the interface assembly further comprises a firing beam drive block defining an elongate opening, wherein the cam cylinder is disposed in the elongate opening, wherein the cam cylinder is structured and positioned to translate the drive block longitudinally in response to rotation of the cam cylinder.

17. The apparatus of claim 1, wherein a first set of the drive shafts is positioned on one lateral side of the shaft assembly, wherein a second set of the drive shafts is positioned on another lateral side of the shaft assembly.

18. The apparatus of claim 1, wherein the surgical end effector comprises at least one electrode structured and positioned to deliver RF energy to tissue.

19. An apparatus for operating on tissue comprising:
(a) a surgical end effector structured and positioned to manipulate tissue;
(b) a shaft assembly in communication with the surgical end effector, wherein the shaft assembly defines a longitudinal axis; and
(c) an interface assembly in communication with the shaft assembly, wherein the interface assembly comprises:
   (i) a housing structured and positioned to rotate and articulate the shaft assembly, and
   (ii) a base having a plurality of drive shafts, wherein the drive shafts are operable independently of each other, wherein the plurality of shafts are configured to engage the housing to drive rotation of the shaft assembly about the longitudinal axis and to drive articulation of the shaft assembly, wherein the plurality of drive shafts are oriented perpendicularly in relation to the longitudinal axis defined by the shaft assembly.

20. An apparatus for operating on tissue, the apparatus comprising:
(a) a surgical end effector, wherein the surgical end effector comprises a clamping jaw feature;
(b) a shaft assembly, wherein the surgical end effector is coupled with the shaft assembly, wherein the shaft assembly comprises a translating member;
(c) a housing assembly, wherein the shaft assembly is secured to the housing assembly, wherein the housing assembly includes an integral rack, wherein the integral rack is translatable relative to the shaft assembly to translate the translating member of the shaft assembly; and (d) a base assembly, wherein the housing assembly is configured to removably couple with the base assembly, wherein the base assembly comprises a drive shaft structured and positioned to drive the integral rack of the housing assembly, wherein the base assembly is configured to couple with a dock of a robotic drive system.

* * * * *

UNITED STATES PATENT AND TRADEMARK OFFICE
CERTIFICATE OF CORRECTION

PATENT NO. : 9,737,300 B2  
APPLICATION NO. : 13/798735  
DATED : August 22, 2017  
INVENTOR(S) : Parihar et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 534 days.

Signed and Sealed this

Twenty-fifth Day of September, 2018

Andrei Iancu
*Director of the United States Patent and Trademark Office*